United States Patent
Tanaka

(10) Patent No.: US 7,252,086 B2
(45) Date of Patent: *Aug. 7, 2007

(54) LUNG REDUCTION SYSTEM

(75) Inventor: Don Tanaka, Saratoga, CA (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/852,271

(22) Filed: May 24, 2004

(65) Prior Publication Data

US 2004/0244802 A1    Dec. 9, 2004

Related U.S. Application Data

(60) Provisional application No. 60/475,291, filed on Jun. 3, 2003.

(51) Int. Cl.
*A61M 16/00* (2006.01)
*A61F 5/44* (2006.01)

(52) U.S. Cl. .......................... 128/200.26; 128/207.14; 604/328

(58) Field of Classification Search ........... 128/200.26, 128/207.14, 207.15, 207.16, 898; 604/509, 604/516, 102.01, 102.02, 328; 606/46; 623/9
See application file for complete search history.

(56) References Cited

U.S. PATENT DOCUMENTS

| | | | | |
|---|---|---|---|---|
| 733,152 | A * | 7/1903 | Chisholm | 604/247 |
| 953,922 | A | 4/1910 | Rogers | 128/207.17 |
| 2,867,213 | A * | 1/1959 | Thomas, Jr. | 604/247 |
| 2,873,742 | A | 2/1959 | Shelden | 128/207.29 |
| 2,991,787 | A | 7/1961 | Shelden et al. | 128/207.17 |
| 3,384,087 | A | 5/1968 | Brummelkamp | 128/207.29 |
| 3,463,159 | A * | 8/1969 | Heimlich | 604/247 |
| 3,511,243 | A | 5/1970 | Toy | 128/207.29 |
| 3,556,103 | A | 1/1971 | Calhoun | 128/207.29 |
| 3,682,166 | A | 8/1972 | Jacobs | 128/205.19 |
| 3,688,773 | A | 9/1972 | Weiss | 128/207.29 |
| 3,777,757 | A * | 12/1973 | Gray et al. | 604/99.04 |
| 3,788,326 | A | 1/1974 | Jacobs | 128/207.15 |
| 3,817,250 | A | 6/1974 | Weiss et al. | 128/207.29 |
| 3,916,903 | A | 11/1975 | Pozzi | 128/207.29 |
| 4,153,058 | A * | 5/1979 | Nehme | 604/167.03 |
| 4,465,062 | A * | 8/1984 | Versaggi et al. | 128/897 |

(Continued)

FOREIGN PATENT DOCUMENTS

| EP | 1 393 760 A1 | 3/2004 |
|---|---|---|
| EP | 1 481 701 A1 | 12/2004 |

OTHER PUBLICATIONS

Heimlich, H., "Respiratory Rehabilitation with Transtracheal Oxygen System, Part I." *Annals of Otology, Rhinology and Laryngology*, Nov./Dec. 1982, 91(6), 643-647.
European Search Report EP 04253234.1 dated Mar. 15, 2006.

*Primary Examiner*—Teena Mitchell
(74) *Attorney, Agent, or Firm*—Carl J. Evens

(57) ABSTRACT

A pulmonary decompression device may be utilized to remove trapped air in the lung or lungs, thereby reducing the volume of diseased lung tissue. A lung reduction device may passively decompress the lung or lungs. In order for the system to be effective, an airtight seal between the parietal and visceral pleurae is required. Chemical pleurodesis is utilized for creating the seal.

2 Claims, 13 Drawing Sheets

U.S. PATENT DOCUMENTS

| | | | |
|---|---|---|---|
| 5,478,333 A * | 12/1995 | Asherman, Jr. | 604/304 |
| 6,059,816 A * | 5/2000 | Moenning | 606/213 |
| 6,287,290 B1 * | 9/2001 | Perkins et al. | 604/516 |
| 6,328,689 B1 * | 12/2001 | Gonzalez et al. | 600/37 |
| 6,330,882 B1 * | 12/2001 | French | 128/200.26 |
| 6,679,264 B1 * | 1/2004 | Deem et al. | 128/207.16 |
| 6,692,494 B1 * | 2/2004 | Cooper et al. | 606/46 |
| 6,886,558 B2 * | 5/2005 | Tanaka | 128/200.26 |
| 6,941,950 B2 * | 9/2005 | Wilson et al. | 128/207.14 |
| 7,195,017 B2 * | 3/2007 | Tanaka | 128/207.14 |
| 2004/0211434 A1 * | 10/2004 | Loomas et al. | 128/898 |
| 2005/0137611 A1 * | 6/2005 | Escudero et al. | 606/108 |

* cited by examiner

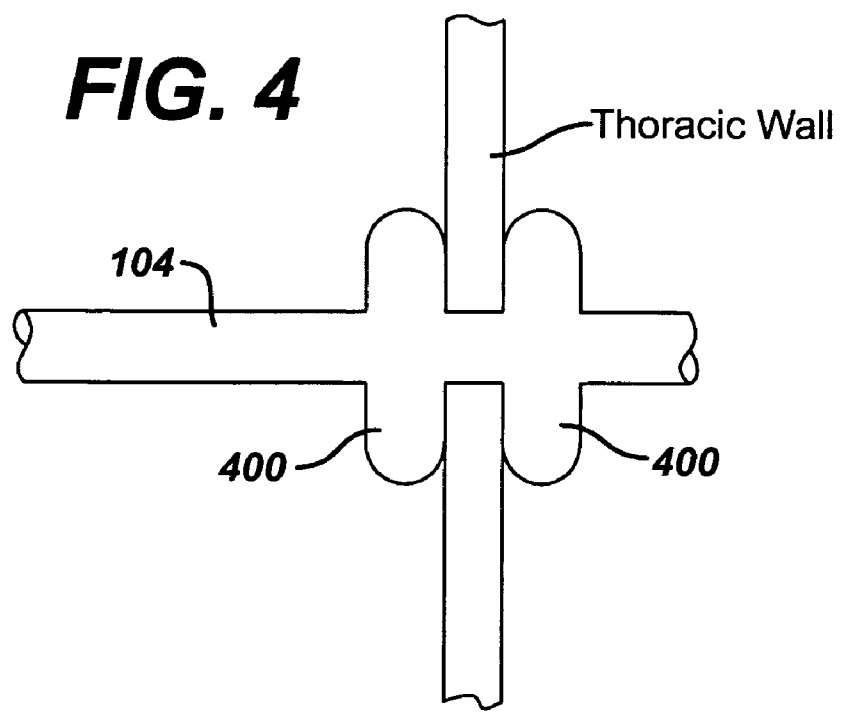
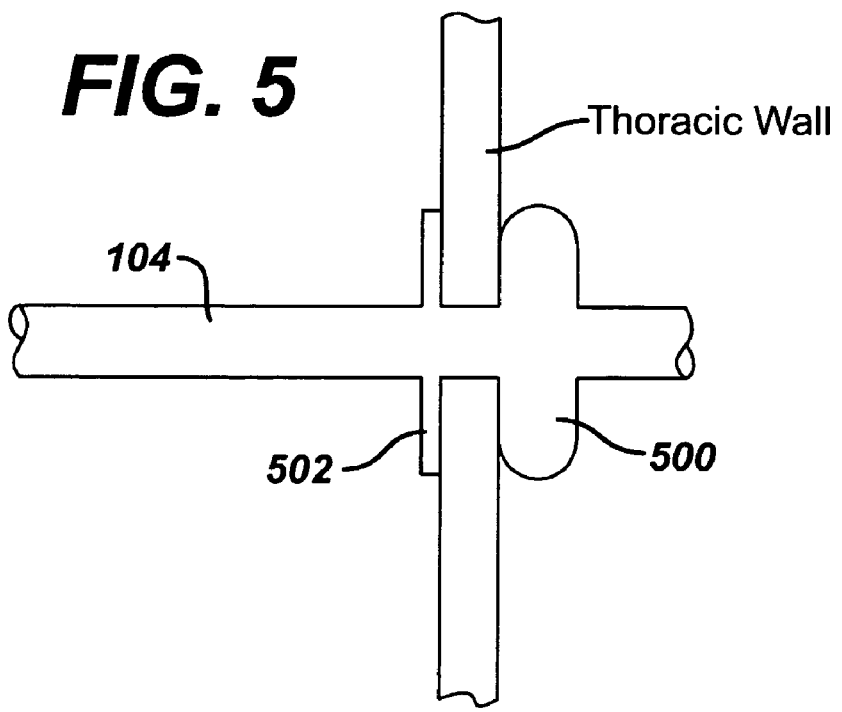

LUNG REDUCTION SYSTEM

CROSS REFERENCE TO RELATED APPLICATIONS

This application claims the benefit of Provisional Application No. 60/475,291 filed Jun. 3, 2003.

BACKGROUND OF THE INVENTION

1. Field of the Invention

The present invention relates to systems and methods for removing trapped air in emphysematous lungs, and more particularly, to systems and methods for removing trapped air in emphysematous hyperinflated lungs by bypassing non-patent airways via a conduit through the outer pleural layer of the lung to a containment/trap device. The present invention also relates to a collateral ventilation bypass system that utilizes the trachea for expelling trapped air rather than a containment/trap device. The present invention also relates to a device and methodology to assist in pulmonary decompression and non-surgical/resection lung volume reduction. The present invention also relates to systems and methods for chemical pleurodesis.

2. Discussion of the Related Art

As a result of studies that date back to the 1930's and particularly studies conducted in the 1960's and early 1970's, it has been determined that long-term continuous oxygen therapy is beneficial in the treatment of hypoxemic patients with chronic obstructive pulmonary disease. In other words, a patient's life and quality of life can be improved by providing a constant supplemental supply of oxygen to the patient's lungs.

However, with the desire to contain medical costs, there is a growing concern that the additional cost of providing continuous oxygen therapy for chronic lung disease will create an excessive increase in the annual cost of oxygen therapy. Thus, it is desirable that oxygen therapy, when provided, be as cost effective as possible.

The standard treatment for patients requiring supplemental oxygen is still to deliver oxygen from an oxygen source by means of a nasal cannula. Such treatment, however, requires a large amount of oxygen, which is wasteful and can cause soreness and irritation to the nose, as well as being potentially aggravating. Other undesirable effects have also been reported. Various other medical approaches which have been proposed to help reduce the cost of continuous oxygen therapy have been studied.

Various devices and methods have been devised for performing emergency cricothyroidotomies and for providing a tracheotomy tube so that a patient whose airway is otherwise blocked may continue to breath. Such devices are generally intended only for use with a patient who is not breathing spontaneously and are not suitable for the long term treatment of chronic lung disease. Typically, such devices are installed by puncturing the skin to create a hole into the cricoid membrane of the larynx above the trachea into which a relatively large curved tracheotomy tube is inserted. As previously described, the use of such tubes has been restricted medically to emergency situations where the patient would otherwise suffocate due to the blockage of the airway. Such emergency tracheotomy tubes are not suitable for long term therapy after the airway blockage is removed.

Other devices which have been found satisfactory for emergency or ventilator use are described in U.S. Pat. Nos. 953,922 to Rogers; 2,873,742 to Shelden; 3,384,087 to Brummelkamp; 3,511,243 to Toy; 3,556,103 to Calhoun; 2,991,787 to Shelden, et al; 3,688,773 to Weiss; 3,817,250 to Weiss, et al.; and 3,916,903 to Pozzi.

Although tracheotomy tubes are satisfactory for their intended purpose, they are not intended for chronic usage by outpatients as a means for delivering supplemental oxygen to spontaneously breathing patients with chronic obstructive pulmonary disease. Such tracheotomy tubes are generally designed so as to provide the total air supply to the patient for a relatively short period of time. The tracheotomy tubes are generally of rigid or semi-rigid construction and of caliber ranging from 2.5 mm outside diameter in infants to 15 mm outside diameter in adults. They are normally inserted in an operating room as a surgical procedure or during emergency situations, through the crico-thyroid membrane where the tissue is less vascular and the possibility of bleeding is reduced. These devices are intended to permit passage of air in both directions until normal breathing has been restored by other means.

Another type of tracheotomy tube is disclosed in Jacobs, U.S. Pat. Nos. 3,682,166 and 3,788,326. The catheter described therein is placed over 14 or 16 gauge needle and inserted through the crico-thyroid membrane for supplying air or oxygen and vacuum on an emergency basis to restore the breathing of a non-breathing patient. The air or oxygen is supplied at 30 to 100 psi for inflation and deflation of the patient's lungs. The Jacobs catheter, like the other tracheotomy tubes previously used, is not suitable for long term outpatient use, and could not easily be adapted to such use.

Due to the limited functionality of tracheotomy tubes, transtracheal catheters have been proposed and used for long term supplemental oxygen therapy. For example the small diameter transtracheal catheter (16 gauge) developed by Dr. Henry J. Heimlich (described in THE ANNALS OF OTOLOGY, RHINOLOGY & LARYNGOLOGY, November-December 1982; Respiratory Rehabilitation with Transtracheal Oxygen System) has been used by the insertion of a relatively large cutting needle (14 gauge) into the trachea at the mid-point between the cricothyroid membrane and the sternal notch. This catheter size can supply oxygen up to about 3 liters per minute at low pressures, such as 2 psi which may be insufficient for patients who require higher flow rates. It does not, however, lend itself to outpatient use and maintenance, such as periodic removal and cleaning, primarily because the connector between the catheter and the oxygen supply hose is adjacent and against the anterior portion of the trachea and cannot be easily seen and manipulated by the patient. Furthermore, the catheter is not provided with positive means to protect against kinking or collapsing which would prevent its effective use on an outpatient basis. Such a feature is not only desirable but necessary for long term outpatient and home care use. Also, because of its structure, i.e. only one exit opening, the oxygen from the catheter is directed straight down the trachea toward the bifurcation between the bronchi. Because of the normal anatomy of the bronchi wherein the left bronchus is at a more acute angle to the trachea than the right bronchus, more of the oxygen from that catheter tends to be directed into the right bronchus rather than being directed or mixed for more equal utilization by both bronchi. Also, as structured, the oxygen can strike the carina, resulting in an undesirable tickling sensation and cough. In addition, in such devices, if a substantial portion of the oxygen is directed against the back wall of the trachea causing erosion of the mucosa in this area which may cause chapping and bleeding. Overall, because of the limited output from the device, it may not operate to supply sufficient supplemental oxygen when the patient is exercising or otherwise quite active or has severe disease.

Diseases associated with chronic obstructive pulmonary disease include chronic bronchitis and emphysema. One aspect of an emphysematous lung is that the communicating flow of air between neighboring air sacs is much more prevalent as compared to healthy lungs. This phenomenon is known as collateral ventilation. Another aspect of an emphysematous lung is that air cannot be expelled from the native airways due to the loss of tissue elastic recoil and radial support of the airways. Essentially, the loss of elastic recoil of the lung tissue contributes to the inability of individuals to exhale completely. The loss of radial support of the airways also allows a collapsing phenomenon to occur during the expiratory phase of breathing. This collapsing phenomenon also intensifies the inability for individuals to exhale completely. As the inability to exhale completely increases, residual volume in the lungs also increases. This then causes the lung to establish in a hyperinflated state where an individual can only take short shallow breaths. Essentially, air is not effectively expelled and stale air accumulates in the lungs. Once the stale air accumulates in the lungs, the individual is deprived of oxygen.

Currently, treatments for chronic obstructive pulmonary disease include bronchodilating drugs, oxygen therapy as described above, and lung volume reduction surgery. Bronchodilating drugs only work on a percentage of patients with chronic obstructive pulmonary disease and generally only provides short term relief. Oxygen therapy is impractical for the reasons described above, and lung volume reduction surgery is an extremely traumatic procedure that involves removing part of the lung. The long term benefits of lung volume reduction surgery are not fully known.

Accordingly, there exists a need for increasing the expiratory flow from an individual suffering from chronic obstructive pulmonary disease. In addition, there exists a need for a minimally invasive means for removing trapped air from the lung or lungs that would allow healthy lung tissue to better ventilate. There also exists a need for a minimally invasive means for allowing trapped air from the lung or lungs to escape that would allow healthy lung tissue to better ventilate.

SUMMARY OF THE INVENTION

The present invention overcomes the disadvantages associated with treating chronic obstructive pulmonary disease, as briefly described above, by utilizing the phenomenon of collateral ventilation to increase the expiratory flow from a diseased lung. The present invention also provides a means for assisting in or facilitating pulmonary decompression to compress the diseased area or area of the lung or lungs to a/smaller volume.

In accordance with a first aspect, the present invention is directed to a lung reduction device. The device comprising at least one first member in fluid communication, at a predetermine site, within a lung of a patient, a sealing device for establishing an airtight seal between the at least one first member and the lung, and a second member connected to the at least one first member, the second member comprising an apparatus for allowing air from the lung of the patient to vent to an area external of the lung and preventing air from an area external of the lung from re-entering the lung through the device.

In accordance with a second aspect, the present invention is directed to a lung reduction device. The device comprising at least one first member in fluid communication, at a predetermined site, within a lung of a patient, a first sealing device for establishing an airtight seal between the at least one first member and the lung, a second member connected to and in fluid communication with the at least one first member, the second member comprising an apparatus for allowing air from the lung of the patient to vent to the ambient environment, and preventing air from the ambient environment from re-entering the lung through the device, the second member including a section positioned external of the body of the patient, and a second sealing device for sealing the section positioned external of the body of the patient to the body.

In accordance with a third aspect, the present invention is directed to a method for reducing the volume of a hyperinflated portion of a lung of a patient. The device comprising determining a site of hyperinflation in a patient's lung, and allowing air from the hyperinflated portion of the lung to vent through a device to the ambient environment and preventing air from the ambient environment from re-entering the lung through the device.

The long-term oxygen therapy system of the present invention delivers oxygen directly to diseased sites in a patient's lungs. Long term oxygen therapy is widely accepted as the standard treatment for hypoxia caused by chronic obstructive pulmonary disease, for example, pulmonary emphysema. Pulmonary emphysema is a chronic obstructive pulmonary disease wherein the alveoli of the lungs lose their elasticity and the walls between adjacent alveoli are destroyed. As more and more alveoli walls are lost, the air exchange surface area of the lungs is reduced until air exchange becomes seriously impaired. The combination of mucus hypersecretion and dynamic air compression is a mechanism of airflow limitation in chronic obstructive pulmonary disease. Dynamic air compression results from the loss of tethering forces exerted on the airway due to the reduction in lung tissue elasticity. Essentially, stale air accumulates in the lungs, thereby depriving the individual of oxygen. Various methods may be utilized to determine the location or locations of the diseased tissue, for example, computerized axial tomography or CAT scans, magnetic resonance imaging or MRI, positron emission tomograph or PET, and/or standard X-ray imaging. Once the location or locations of the diseased tissue are located, anastomotic openings are made in the thoracic cavity and lung or lungs and one or more oxygen carrying conduits are positioned and sealed therein. The one or more oxygen carrying conduits are connected to an oxygen source which supplies oxygen under elevated pressure directly to the diseased portion or portions of the lung or lungs. The pressurized oxygen essentially displaces the accumulated air and is thus more easily absorbed by the alveoli tissue. In addition, the long term oxygen therapy system may be configured in such a way as to provide collateral ventilation bypass in addition to direct oxygen therapy. In this configuration, an additional conduit may be connected between the main conduit and the individual's trachea with the appropriate valve arrangement. In this configuration, stale air may be removed through the trachea when the individual exhales since the trachea is directly linked with the diseased site or sites in the lung via the conduits.

The long term oxygen therapy system of the present invention improves oxygen transfer efficiency in the lungs thereby reducing oxygen supply requirements, which in turn reduces the patient's medical costs. The system also allows for improved self-image, improved mobility, greater exercise capability and is easily maintained.

The above-described long term oxygen therapy system may be utilized to effectively treat hypoxia caused by chronic obstructive pulmonary disease; however, other means may be desirable to treat other aspects of the disease. As set forth above, emphysema is distinguished as irreversible damage to lung tissue. The breakdown of lung tissue leads to the reduced ability for the lungs to recoil. The tissue breakdown also leads to the loss of radial support of the airways. Consequently, the loss of elastic recoil of the lung tissue contributes to the inability for individuals with emphysema to exhale completely. The loss of radial support of the airways also allows a collapsing phenomenon to occur during the expiratory phase of breathing. This collapsing phenomenon also intensifies the inability for individuals to exhale completely. As the inability to exhale increases, residual volume in the lungs also increases. This then causes the lung to establish in a hyperinflated state wherein an individual can only take short shallow breaths.

The collateral ventilation bypass trap system of the present invention utilizes the above-described collateral ventilation phenomenon to increase the expiratory flow from a diseased lung or lungs, thereby treating another aspect of chronic obstructive pulmonary disease. Essentially, the most collaterally ventilated area of the lung or lungs is determined utilizing the scanning techniques described above. Once this area or areas are located, a conduit or conduits are positioned in a passage or passages that access the outer pleural layer of the diseased lung or lungs. The conduit or conduits utilize the collateral ventilation of the lung or lungs and allow the entrapped air to bypass the native airways and be expelled to a containment system outside of the body.

In an alternate embodiment, the trachea, or other proximal airways, including the bronchus, may be utilized for expelling trapped air rather than a containment/trap device.

The pulmonary decompression device of the present invention removes air from hyperinflated regions of the lung or lungs of a patient by creating a slight pressure differential between the internal volume of the lung and a location external of the lung. An apparatus such as a vacuum fan or pump creates the pressure differential, thereby removing the trapped air and reducing the volume of diseased tissue.

The lung reduction device of the present invention allows trapped air from hyperinflated regions of the lung or lungs of a patient to vent to the external environment through a one-way valve. The valve prevents air from flowing back into the lung or lungs.

In order for the system to be effective, the components of the system are preferably sealed to the lung. Accordingly, the localized pleurodesis chemical delivery system of the present invention is utilized to create a pleurodesis in the area or areas of the lung that are most collaterally ventilated. Various chemicals, agents and/or compounds may be delivered via catheter based delivery systems or via implantable medical devices.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 4 is a diagrammatic representation of a third exemplary embodiment of a sealing device utilized in conjunction with the long term oxygen therapy system of the present invention.

FIG. 5 is a diagrammatic representation of a fourth exemplary embodiment of a sealing device utilized in conjunction with the long term oxygen therapy system of the present invention.

DETAILED DESCRIPTION OF THE PREFERRED EMBODIMENTS

Figure 1:
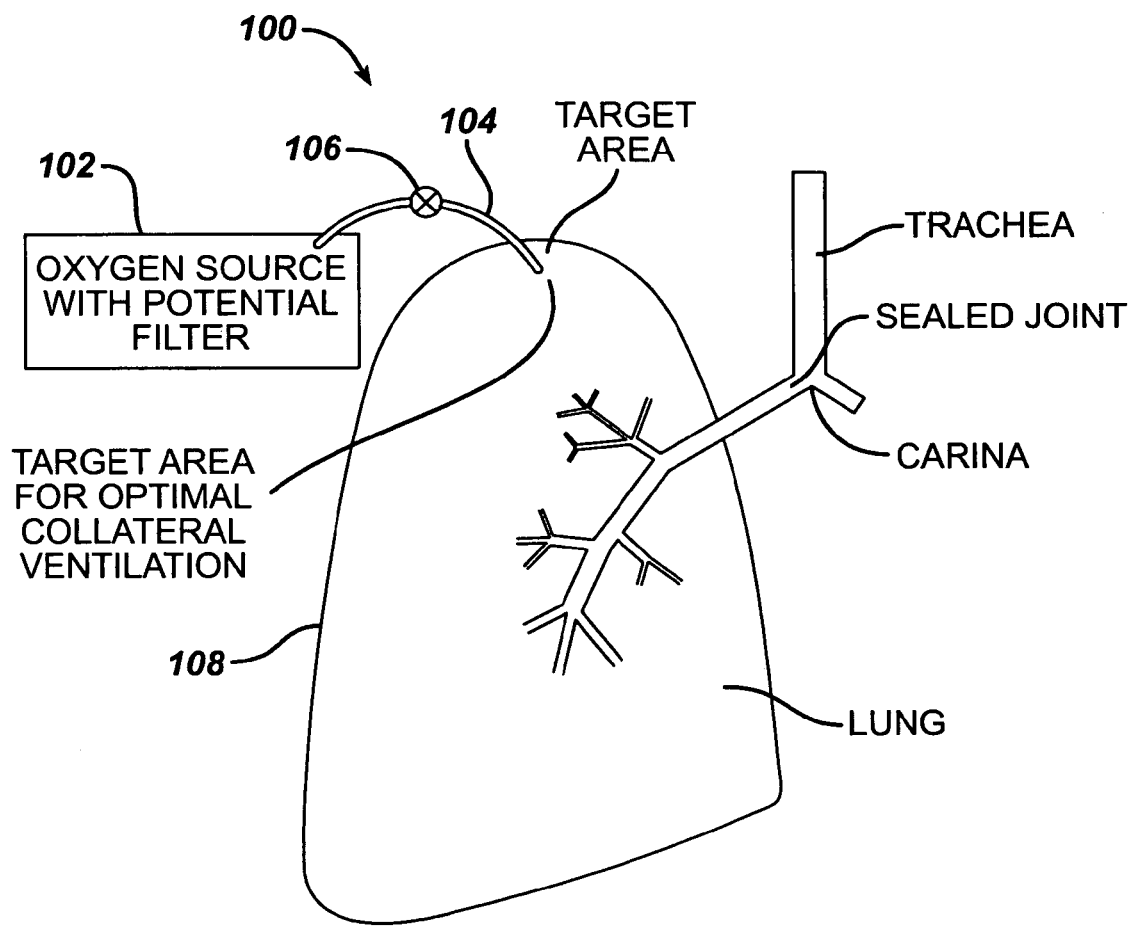
FIG. 1 is a diagrammatic representation of a first exemplary embodiment of the long term oxygen therapy system in accordance with the present invention.

Air typically enters the mammalian body through the nostrils and flows into the nasal cavities. As the air passes through the nostrils and nasal cavities, it is filtered, moistened and raised or lowered to approximately body temperature. The back of the nasal cavities is continuous with the pharynx (throat region); therefore, air may reach the pharynx from the nasal cavities or from the mouth. Accordingly, if equipped, the mammal may breath through its nose or mouth. Generally air from the mouth is not as filtered or temperature regulated as air from the nostrils. The air in the pharynx flows from an opening in the floor of the pharynx and into the larynx (voice box). The epiglottis automatically closes off the larynx during swallowing so that solids and/or liquids enter the esophagus rather than the lower air passageways or airways. From the larynx, the air passes into the trachea, which divides into two branches, referred to as the bronchi. The bronchi are connected to the lungs.

The lungs are large, paired, spongy, elastic organs, which are positioned in the thoracic cavity. The lungs are in contact with the walls of the thoracic cavity. In humans, the right lung comprises three lobes and the left lung comprises two lobes. Lungs are paired in all mammals, but the number of lobes or sections of lungs varies from mammal to mammal. Healthy lungs, as discussed below, have a tremendous surface area for gas/air exchange. Both the left and right lung is covered with a pleural membrane. Essentially, the pleural membrane around each lung forms a continuous sac that encloses the lung. A pleural membrane also forms a lining for the thoracic cavity. The space between the pleural membrane forming the lining of the thoracic cavity and the pleural membranes enclosing the lungs is referred to as the pleural cavity. The pleural cavity comprises a film of fluid that serves as a lubricant between the lungs and the chest wall.

In the lungs, the bronchi branch into a multiplicity of smaller vessels referred to as bronchioles. Typically, there are more than one million bronchioles in each lung. Each bronchiole ends in a cluster of extremely small air sacs referred to as alveoli. An extremely thin, single layer of epithelial cells lining each alveolus wall and an extremely thin, single layer of epithelial cells lining the capillary walls separate the air/gas in the alveolus from the blood. Oxygen molecules in higher concentration pass by simple diffusion through the two thin layers from the alveoli into the blood in the pulmonary capillaries. Simultaneously, carbon dioxide molecules in higher concentration pass by simple diffusion through the two thin layers from the blood in the pulmonary capillaries into the alveoli.

Breathing is a mechanical process involving inspiration and expiration. The thoracic cavity is normally a closed system and air cannot enter or leave the lungs except through the trachea. If the chest wall is somehow compromised and air/gas enters the pleural cavity, the lungs will typically collapse. When the volume of the thoracic cavity is increased by the contraction of the diaphragm, the volume of the lungs is also increased. As the volume of the lungs increase, the pressure of the air in the lungs falls slightly below the pressure of the air external to the body (ambient air pressure). Accordingly, as a result of this slight pressure differential, external or ambient air flows through the respiratory passageways described above and fills the lungs until the pressure equalizes. This process is inspiration. When the diaphragm is relaxed, the volume of the thoracic cavity decreases, which in turn decreases the volume of the lungs. As the volume of the lungs decrease, the pressure of the air in the lungs rises slightly above the pressure of the air external to the body. Accordingly, as a result of this slight pressure differential, the air in the alveoli is expelled through the respiratory passageways until the pressure equalizes. This process is expiration.

Continued insult to the respiratory system may result in various diseases, for example, chronic obstructive pulmonary disease. Chronic obstructive pulmonary disease is a persistent obstruction of the airways caused by chronic bronchitis and pulmonary emphysema. In the United States alone, approximately fourteen million people suffer from some form of chronic obstructive pulmonary disease and it is in the top ten leading causes of death.

Chronic bronchitis and acute bronchitis share certain similar characteristics; however, they are distinct diseases. Both chronic and acute bronchitis involve inflammation and constriction of the bronchial tubes and the bronchioles; however, acute bronchitis is generally associated with a viral and/or bacterial infection and its duration is typically much shorter than chronic bronchitis. In chronic bronchitis, the bronchial tubes secrete too much mucus as part of the body's defensive mechanisms to inhaled foreign substances. Mucus membranes comprising ciliated cells (hair like structures) line the trachea and bronchi. The ciliated cells or cilia continuously push or sweep the mucus secreted from the mucus membranes in a direction away from the lungs and into the pharynx, where it is periodically swallowed. This sweeping action of the cilia functions to keep foreign matter from reaching the lungs. Foreign matter that is not filtered by the nose and larynx, as described above, becomes trapped in the mucus and is propelled by the cilia into the pharynx. When too much mucus is secreted, the ciliated cells may become damaged, leading to a decrease in the efficiency of the cilia to sweep the bronchial tubes and trachea of the mucus containing the foreign matter. This in turn causes the bronchioles to become constricted and inflamed and the individual becomes short of breath. In addition, the individual will develop a chronic cough as a means of attempting to clear the airways of excess mucus.

Individuals who suffer from chronic bronchitis may develop pulmonary emphysema. Pulmonary emphysema is a disease in which the alveoli walls, which are normally fairly rigid structures, are destroyed. The destruction of the alveoli walls is irreversible. Pulmonary emphysema may be caused by a number of factors, including chronic bronchitis, long term exposure to inhaled irritants, e.g. air pollution, which damage the cilia, enzyme deficiencies and other pathological conditions. In pulmonary emphysema, the alveoli of the lungs lose their elasticity, and eventually the walls between adjacent alveoli are destroyed. Accordingly, as more and more alveoli walls are lost, the air exchange (oxygen and carbon dioxide) surface area of the lungs is reduced until air exchange becomes seriously impaired. The combination of mucus hypersecretion and dynamic airway compression are mechanisms of airflow limitation in chronic obstructive pulmonary disease. Dynamic airway compression results from the loss of tethering forces exerted on the airway due to the reduction in lung tissue elasticity. Mucus hypersecretion is described above with respect to bronchitis. In other words, the breakdown of lung tissue leads to the reduced ability of the lungs to recoil and the loss of radial support of the airways. Consequently, the loss of elastic recoil of the lung tissue contributes to the inability of individuals to exhale completely. The loss of radial support of the airways also allows a collapsing phenomenon to occur during the expiratory phase of breathing. This collapsing phenomenon also intensifies the inability for individuals to exhale completely. As the inability to exhale completely increases, residual volume in the lungs also increases. This then causes the lung to establish in a hyperinflated state where an individual can only take short shallow breaths. Essentially, air is not effectively expelled and stale air accumulates in the lungs. Once the stale air accumulates in the lungs, the individual is deprived of oxygen. There is no cure for pulmonary emphysema, only various treatments, including exercise, drug therapy, such as bronchodilating agents, lung volume reduction surgery and long term oxygen therapy.

As described above, long term oxygen therapy is widely accepted as the standard treatment for hypoxia caused by chronic obstructive pulmonary disease. Typically, oxygen therapy is prescribed using a nasal cannula. There are disadvantages associated with using the nasal cannula. One disadvantage associated with utilizing nasal cannula is the significant loss of oxygen between the cannula and the nose, which in turn equates to more frequent changes in the oxygen source, or higher energy requirements to generate more oxygen. Another disadvantage associated with utilizing nasal cannula is the fact that the cannulas may cause the nasal passages to become dry, cracked and sore.

Transtracheal oxygen therapy has become a viable alternative to long term oxygen therapy. Transtracheal oxygen therapy delivers oxygen directly to the lungs using a catheter that is placed through and down the trachea. Due to the direct nature of the oxygen delivery, a number of advantages are achieved. These advantages include lower oxygen requirements due to greater efficiency, increased mobility, greater exercise capability and improved self image.

The long term oxygen therapy system and method of the present invention may be utilized to deliver oxygen directly into the lung tissue in order to optimize oxygen transfer efficiency in the lungs. In other words, improved efficiency may be achieved if oxygen were to be delivered directly into the alveolar tissue in the lungs. In emphysema, alveoli walls are destroyed, thereby causing a decrease in air exchange surface area. As more alveoli walls are destroyed, collateral ventilation resistance is lowered. In other words, pulmonary emphysema causes an increase in collateral ventilation and to a certain extent, chronic bronchitis also causes an increase in collateral ventilation. Essentially, in an emphysematous lung, the communicating flow of air between neighboring air sacs (alveoli), known as collateral ventilation, is much more prevalent as compared to a normal lung. Since air cannot be expelled from the native airways due to the loss of tissue elastic recoil and radial support of the airways (dynamic collapse during exhalation), the increase in collateral ventilation does not significantly assist an individual in breathing. The individual develops dsypnea. Accordingly, if it can be determined where collateral ventilation is occurring, then the diseased lung tissue may be isolated and the oxygen delivered to this precise location or locations. Various methods may be utilized to determine the diseased tissue locations, for example, computerized axial tomography or CAT scans, magnetic resonance imaging or MRI, positron emission tomograph or PET, and/or standard X-ray imaging. Once the diseased tissue is located, pressurized oxygen may be directly delivered to these diseased areas and more effectively and efficiently forced into the lung tissue for air exchange.

FIG. 1 illustrates a first exemplary long term oxygen therapy system 100. The system 100 comprises an oxygen source 102, an oxygen carrying conduit 104 and a one-way valve 106. The oxygen source 102 may comprise any suitable device for supplying filtered oxygen under adjustably regulated pressures and flow rates, including pressurized oxygen tanks, liquid oxygen reservoirs, oxygen concentrators and the associated devices for controlling pressure and flow rate e.g. regulators. The oxygen carrying conduit 104 may comprise any suitable biocompatible tubing having a high resistance to damage caused by continuous oxygen exposure. The oxygen carrying conduit 104 comprises tubing having an inside diameter in the range from about 1/16 inch to about 1/2 inch and more preferably from about 1/8 inch to about 1/4 inch. The one-way valve 106 may comprise any suitable, in-line mechanical valve which allows oxygen to flow into the lungs 108 through the oxygen carrying conduit 104, but not from the lungs 108 back into the oxygen source 102. For example, a simple check valve may be utilized. As illustrated in FIG. 1, the oxygen carrying conduit 104 passes through the lung 108 at the site determined to have the highest degree of collateral ventilation.

The exemplary system 100 described above may be modified in a number of ways, including the use of an in-line filter. In this exemplary embodiment, both oxygen and air may flow through the system. In other words, during inhalation, oxygen is delivered to the lungs through the oxygen carrying conduit 104 and during exhalation, air from the lungs flow through the oxygen carrying conduit 104. The in-line filter would trap mucus and other contaminants, thereby preventing a blockage in the oxygen source 102. In this exemplary embodiment, no valve 106 would be utilized. The flow of oxygen into the lungs and the flow of air from the lungs is based on pressure differentials.

In order for the exemplary long term oxygen therapy system 100 to function, an airtight seal is preferably maintained where the oxygen carrying conduit 104 passes through the thoracic cavity and lung. This seal is maintained in order to sustain the inflation/functionality of the lungs. If the seal is breached, air can enter the cavity and cause the lungs to collapse as described above.

A method to create this seal comprises forming adhesions between the visceral pleura of the lung and the inner wall of the thoracic cavity. This may be achieved using either chemical methods, including irritants such as Doxycycline and/or Bleomycin, surgical methods, including pleurectomy or horoscope talc pleurodesis, or radiotherapy methods, including radioactive gold or external radiation. All of these methods are known in the relevant art for creating pleurodesis. With a seal created at the site for the ventilation bypass, an intervention may be safely performed without the danger of creating a pneumothorax of the lung.

Figure 2:
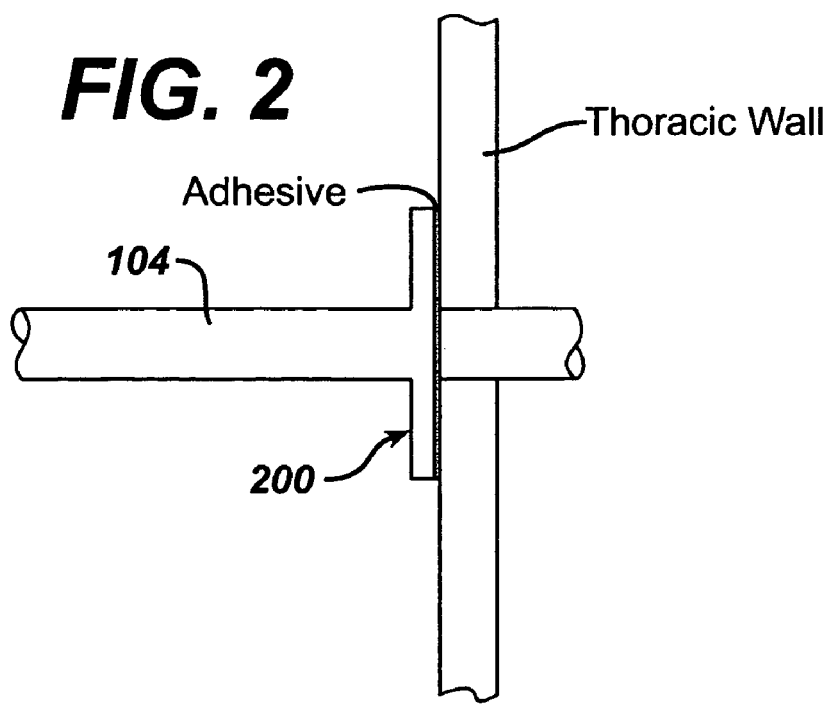
FIG. 2 is a diagrammatic representation of a first exemplary embodiment of a sealing device utilized in conjunction with the long term oxygen therapy system of the present invention.

Similarly to ostomy pouches or bags, the oxygen carrying conduit 104 may be sealed to the skin at the site of the ventilation bypass. In one exemplary embodiment, illustrated in FIG. 2, the oxygen carrying conduit 104 may be sealed to the skin of the thoracic wall utilizing an adhesive. As illustrated, the oxygen carrying conduit 104 comprises a flange 200 having a biocompatible adhesive coating on the skin contacting surface. The biocompatible adhesive would provide a fluid tight seal between the flange 200 and the skin or epidermis of the thoracic wall. In a preferred embodiment, the biocompatible adhesive provides a temporary fluid tight seal such that the oxygen carrying conduit 104 may be disconnected from the ventilation bypass site. This would allow for the site to be cleaned and for the long term oxygen therapy system 100 to undergo periodic maintenance.

Figure 3:
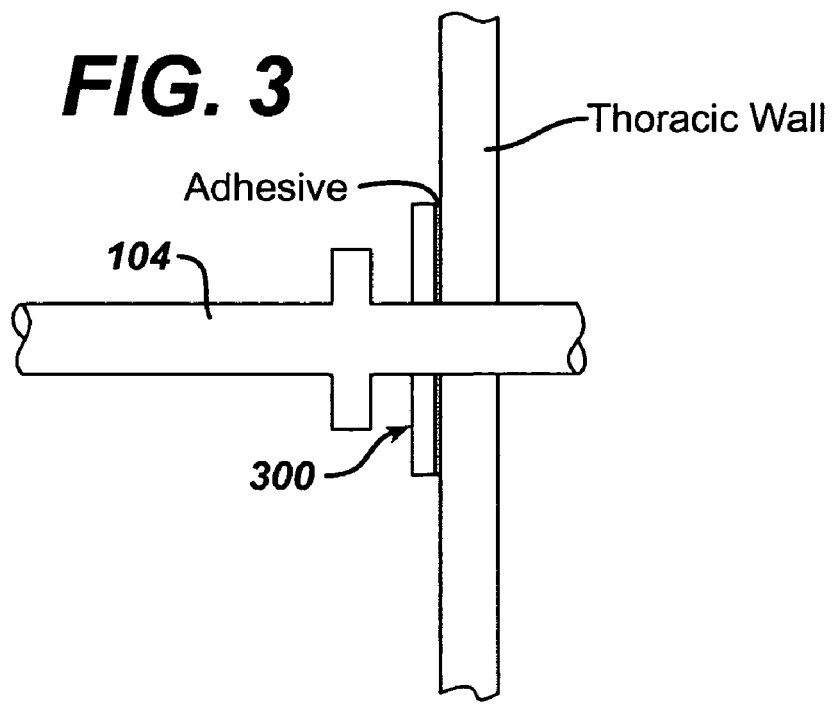
FIG. 3 is a diagrammatic representation of a second exemplary embodiment of a sealing device utilized in conjunction with the long term oxygen therapy system of the present invention.

FIG. 3 illustrates another exemplary embodiment for sealing the oxygen carrying conduit 104 to the skin of the thoracic wall at the site of the ventilation bypass. In this exemplary embodiment, a coupling plate 300 is sealed to the skin at the site of the ventilation bypass by a biocompatible adhesive coating or any other suitable means. The oxygen carrying conduit 104 is then connected to the coupling plate 300 by any suitable means, including threaded couplings and locking rings. The exemplary embodiment also allows for cleaning of the site and maintenance of the system 100.

FIG. 4 illustrates yet another exemplary embodiment for sealing the oxygen carrying conduit 104 to the skin of the thoracic wall at the site of the ventilation bypass. In this exemplary embodiment, balloon flanges 400 may be utilized to create the seal. The balloon flanges 400 may be attached to the oxygen carrying conduit 104 such that in the deflated state, the oxygen carrying conduit 104 and one of the balloon flanges passes through the ventilation bypass anastomosis. The balloon flanges 400 are spaced apart a sufficient distance such that the balloon flanges remain on opposite sides of the thoracic wall. When inflated, the balloons expand and form a fluid tight seal by sandwiching the thoracic wall. Once again, this exemplary embodiment allows for easy removal of the oxygen carrying conduit 104.

FIG. 5 illustrates yet another exemplary embodiment for sealing the oxygen carrying conduit 104 to the skin of the thoracic wall at the site of the ventilation bypass. In this exemplary embodiment, a single balloon flange 500 is utilized in combination with a fixed flange 502. The balloon flange 500 is connected to the oxygen carrying conduit 104 in the same manner as described above. In this exemplary embodiment, the balloon flange 500, when inflated, forms the fluid tight seal. The fixed flange 502, which is maintained against the skin of the thoracic wall, provides the structural support against which the balloon exerts pressure to form the seal.

Figure 6:
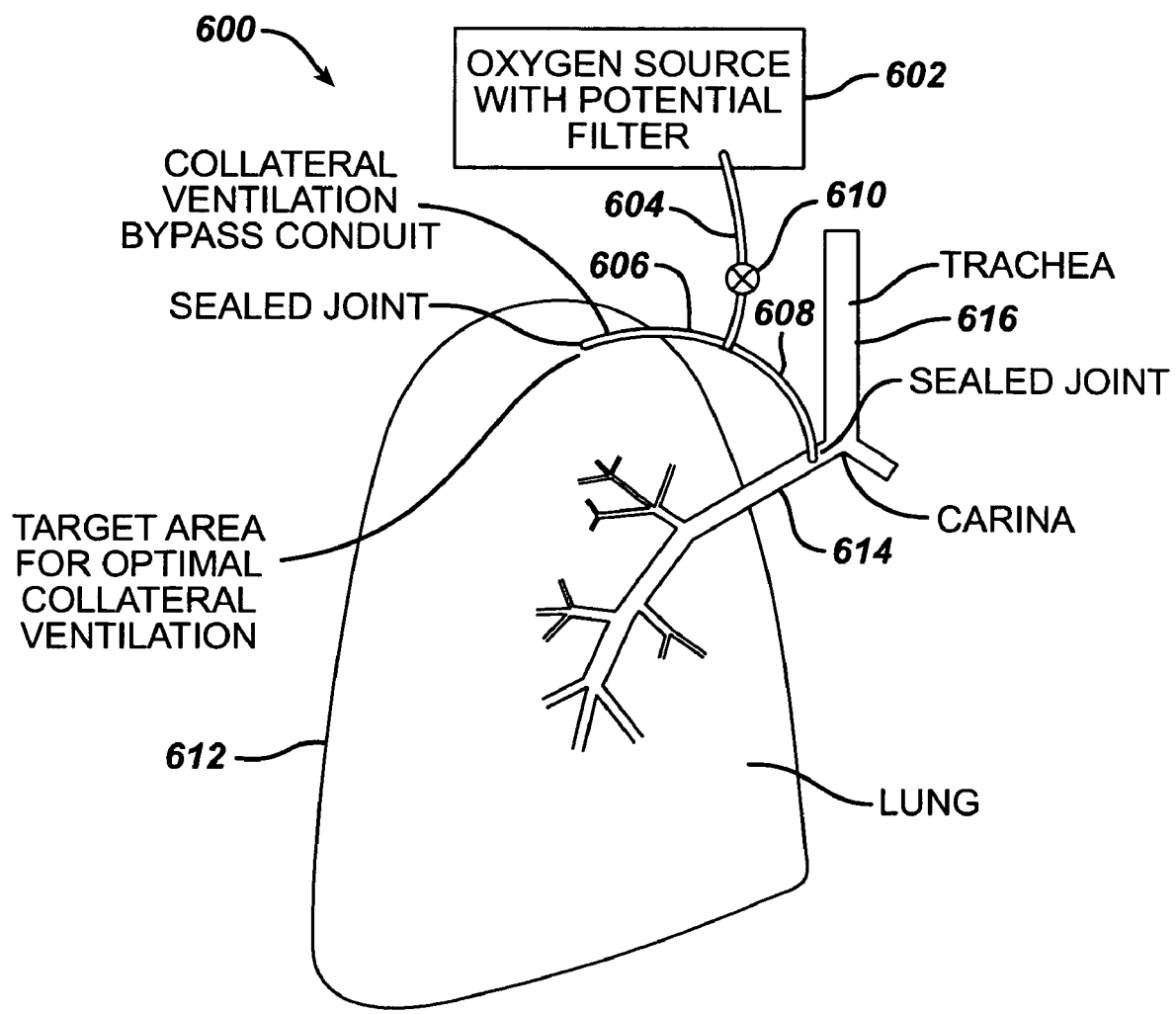
FIG. 6 is a diagrammatic representation of a second exemplary embodiment of the long term oxygen therapy system in accordance with the present invention.

If an individual has difficulty exhaling and requires additional oxygen, collateral ventilation bypass may be combined with direct oxygen therapy. FIG. 6 illustrates an exemplary embodiment of a collateral ventilation bypass/direct oxygen therapy system 600. The system 600 comprises an oxygen source 602, an oxygen carrying conduit 604 having two branches 606 and 608, and a control valve 610. The oxygen source 602 and oxygen carrying conduit 604 may comprise components similar to the above-described exemplary embodiment illustrated in FIG. 1. In this exemplary embodiment, when the individual inhales, the valve 610 is open and oxygen flows into the lung 612 and into the bronchial tube 614. In an alternate exemplary embodiment, the branch 608 may be connected to the trachea 616. Accordingly, during inhalation oxygen flows to the diseased site in the lung or lungs and to other parts of the lung through the normal bronchial passages. During exhalation, the valve 610 is closed so that no oxygen is delivered and air in the diseased portion of the lung may flow from the lung 612, through one branch 606 and into the second branch 608 and finally into the bronchial tube 614. In this manner, stale air is removed and oxygen is directly delivered. Once again, as described above, the flow of oxygen and air is regulated by simple pressure differentials.

The connection and sealing of the oxygen carrying conduit 604 and branches 606, 608 to the lung 612 and bronchial tube 614 may be made in a manner similar to that described above.

The above-described long term oxygen therapy system may be utilized to effectively treat hypoxia caused by chronic obstructive pulmonary disease; however, other means may be desirable to treat other aspects of the disease. As set forth above, emphysema is distinguished as irreversible damage to lung tissue. The breakdown of lung tissue leads to the reduced ability for the lungs to recoil. The tissue breakdown also leads to the loss of radial support of the native airways. Consequently, the loss of elastic recoil of the lung tissue contributes to the inability for individuals with emphysema to exhale completely. The loss of radial support of the native airways also allows a collapsing phenomenon to occur during the expiratory phase of breathing. This collapsing phenomenon also intensifies the inability for individuals to exhale completely. As the inability to exhale increases, residual volume in the lungs also increases. This then causes the lung to establish in a hyperinflated state wherein an individual can only take short shallow breaths.

The collateral ventilation bypass trap system of the present invention utilizes the above-described collateral ventilation phenomenon to increase the expiratory flow from a diseased lung or lungs, thereby treating another aspect of chronic obstructive pulmonary disease. Essentially, the most collaterally ventilated area of the lung or lungs is determined utilizing the scanning techniques described above. Once this area or areas are located, a conduit or conduits are positioned in a passage or passages that access the outer pleural layer of the diseased lung or lungs. The conduit or conduits utilize the collateral ventilation of the lung or lungs and allows the entrapped air to bypass the native airways and be expelled to a containment system outside of the body.

Figure 7:
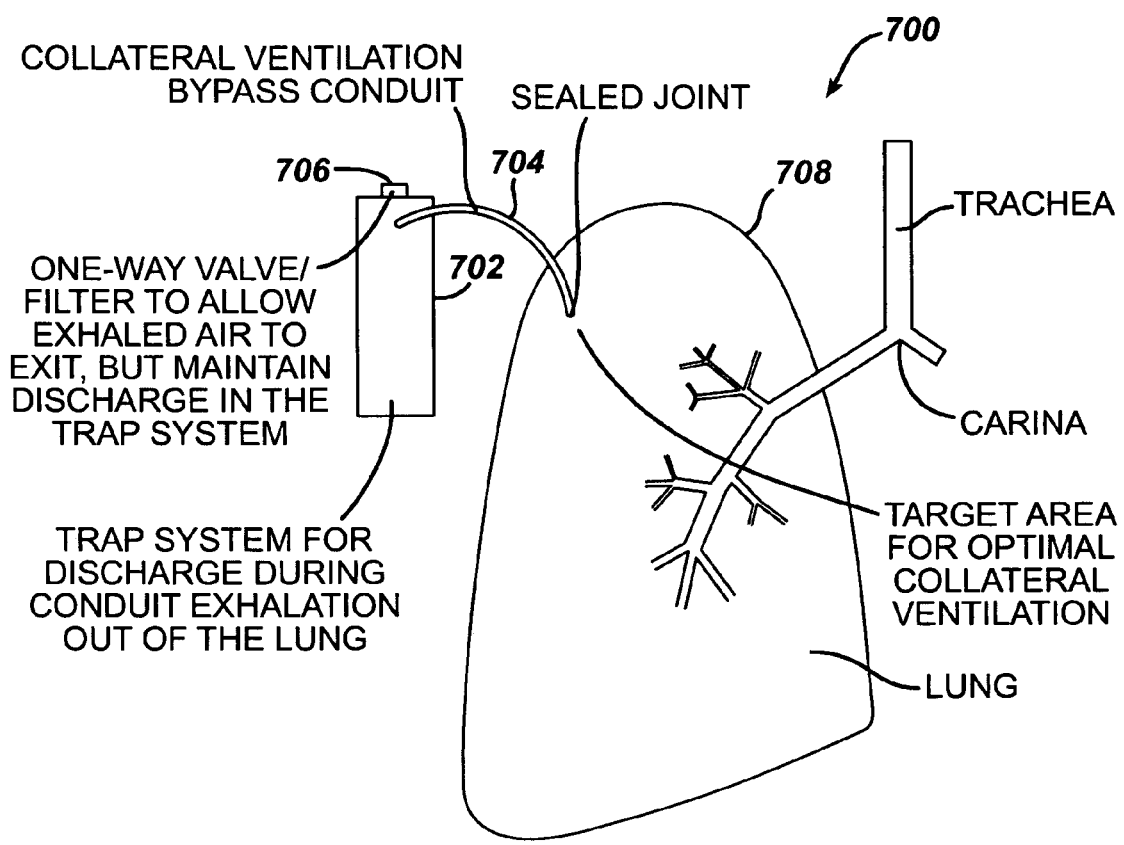
FIG. 7 is a diagrammatic representation of a first exemplary embodiment of a collateral ventilation bypass trap system in accordance with the present invention.

FIG. 7 illustrates a first exemplary collateral ventilation bypass trap system 700. The system 700 comprises a trap 702, an air carrying conduit 704 and a filter/one-way valve 706. The air carrying conduit 704 creates a fluid communication between an individual's lung 708 and the trap 702 through the filter/one-way valve 706. It is important to note that although a single conduit 704 is illustrated, multiple conduits may be utilized in each lung 708 if it is determined that there is more than one area of high collateral ventilation.

The trap 702 may comprise any suitable device for collecting discharge from the individual's lung or lungs 708. Essentially, the trap 702 is simply a containment vessel for temporarily storing discharge from the lungs, for example, mucous and other fluids that may accumulate in the lungs. The trap 702 may comprise any suitable shape and may be formed from any suitable metallic or non-metallic materials. Preferably, the trap 702 should be formed from a lightweight, non-corrosive material. In addition, the trap 702 should be designed in such a manner as to allow for effective and efficient cleaning. In one exemplary embodiment, the trap 702 may comprise disposable liners that may be removed when the trap 702 is full. The trap 702 may be formed from a transparent material or comprise an indicator window so that it may be easily determined when the trap 702 should be emptied or cleaned. A lightweight trap 702 increases the patient's mobility.

The filter/one-way valve 706 may be attached to the trap 702 by any suitable means, including threaded fittings or compression type fittings commonly utilized in compressor connections. The filter/one-way valve 706 serves a number of functions. The filter/one-way valve 706 allows the air from the individual's lung or lungs 708 to exit the trap 702 while maintaining the fluid discharge and solid particulate matter in the trap 702. This filter/one-way valve 706 would essentially maintain the pressure in the trap 702 below that of the pressure inside the individual's lung or lungs 708 so that the flow of air from the lungs 708 to the trap 702 is maintained in this one direction. The filter portion of the filter/one-way valve 706 may be designed to capture particulate matter of a particular size which is suspended in the air, but allows the clean air to pass therethrough and be vented to the ambient environment. The filter portion may also be designed in such a manner as to reduce the moisture content of the exhaled air.

The air carrying conduit 704 connects the trap 702 to the lung or lungs 708 of the patient through the filter/one-way valve 706. The air carrying conduit 704 may comprise any suitable biocompatible tubing having a resistance to the gases contained in air. The air carrying conduit 704 comprises tubing having an inside diameter in the range from about 1/16 inch to about 1/2 inch, and more preferably from about 1/8 inch to about 1/4 inch. The filter/one-way valve 706 may comprise any suitable valve which allows air to flow from the lung or lungs 708 through the air carrying conduit 704, but not from the trap 702 back to the lungs 708. For example, a simple check valve may be utilized. The air carrying conduit 704 may be connected to the filter/one-way valve 706 by any suitable means. Preferably, a quick release mechanism is utilized so that the trap may be easily removed for maintenance. As illustrated in FIG. 7, the air carrying conduit 704 passes through the lung 708 at the site determined to have the highest degree of collateral ventilation. If more than one site is determined, multiple air carrying conduits 704 may be utilized. The connection of multiple air carrying conduits 704 to the filter/one-way valve 706 may be accomplished by any suitable means, including an octopus device similar to that utilized in scuba diving regulators.

The air carrying conduit 704 is preferably able to withstand and resist collapsing once in place. Since air will travel through the conduit 704, if the conduit is crushed and unable to recover, the effectiveness of the system is diminished. Accordingly, a crush recoverable material may be incorporated into the air carrying conduit 704 in order to make it crush recoverable. Any number of suitable materials may be utilized. For example, Nitinol incorporated into the conduit 704 will give the conduit collapse resistance and collapse recovery properties.

Expandable features at the end of the conduit 704 may be used to aid in maintaining contact and sealing the conduit 704 to the lung pleura. Nitinol incorporated into the conduit 704 will provide the ability to deliver the conduit 704 in a compressed state and then deployed in an expanded state to secure it in place. Shoulders at the end of the conduit may also provide a mechanical stop for insertion and an area for an adhesive/sealant to join as described in detail subsequently.

In order for the exemplary collateral ventilation bypass trap system 700 to function, an airtight seal is preferably maintained where the air carrying conduit 704 passes through the thoracic cavity and lungs 708. This seal is maintained in order to sustain the inflation/functionality of the lungs. If the seal is breached, air can enter the cavity and cause the lungs to collapse. One exemplary method for creating the seal comprises forming adhesions between the visceral pleura of the lung and the inner wall of the thoracic cavity. This may be achieved using either chemical methods, including irritants such as Doxycycline and/or Bleomycin, surgical methods, including pleurectomy or thorascopic talc pleurodesis, or radiotherapy methods, including radioactive gold or external radiation. All of these methods are known in the relevant art for creating pleurodesis. In another alternate exemplary embodiment, a sealed joint between the air carrying conduit 704 and the outer pleural layer includes using various glues to help with the adhesion/sealing of the air carrying conduit 704. Currently, Focal Inc. markets a sealant available under the tradename Focal/Seal-L which is indicated for use on a lung for sealing purposes. Focal/Seal-L is activated by light in order to cure the sealant. Another seal available under the tradename Thorex, which is manufactured by Surgical Sealants Inc., is currently conducting a clinical trial for lung sealing indications. Thorex is a two-part sealant that has a set curing time after the two parts are mixed.

The creation of the opening in the chest cavity may be accomplished in a number of ways. For example, the procedure may be accomplished using an open chest procedure, aternotomy or thoracotomy. Alternately, the procedure may be accomplished using a laproscopic technique, which is less invasive. Regardless of the procedure utilized, the seal should be established while the lung is at least partially inflated in order to maintain a solid adhesive surface. The opening may then be made after the joint has been adequately created between the conduit component and the lung pleural surface. The opening should be adequate in cross-sectional area in order to provide sufficient decompression of the hyperinflated lung. This opening, as stated above, may be created using a number of different techniques such as cutting, piercing, dilating, blunt dissection, radio frequency energy, ultrasonic energy, microwave energy, or cryoblative energy.

The air carrying conduit 704 may be sealed to the skin at the site by any of the means and methods described above with respect to the oxygen carrying conduit 704 and illustrated in FIGS. 2 through 5.

In operation, when an individual exhales, the pressure in the lungs is greater than the pressure in the trap 702. Accordingly, the air in the highly collaterilized areas of the lung will travel through the air carrying conduit 704 to the trap 702. This operation will allow the individual to more easily and completely exhale.

Figure 8:
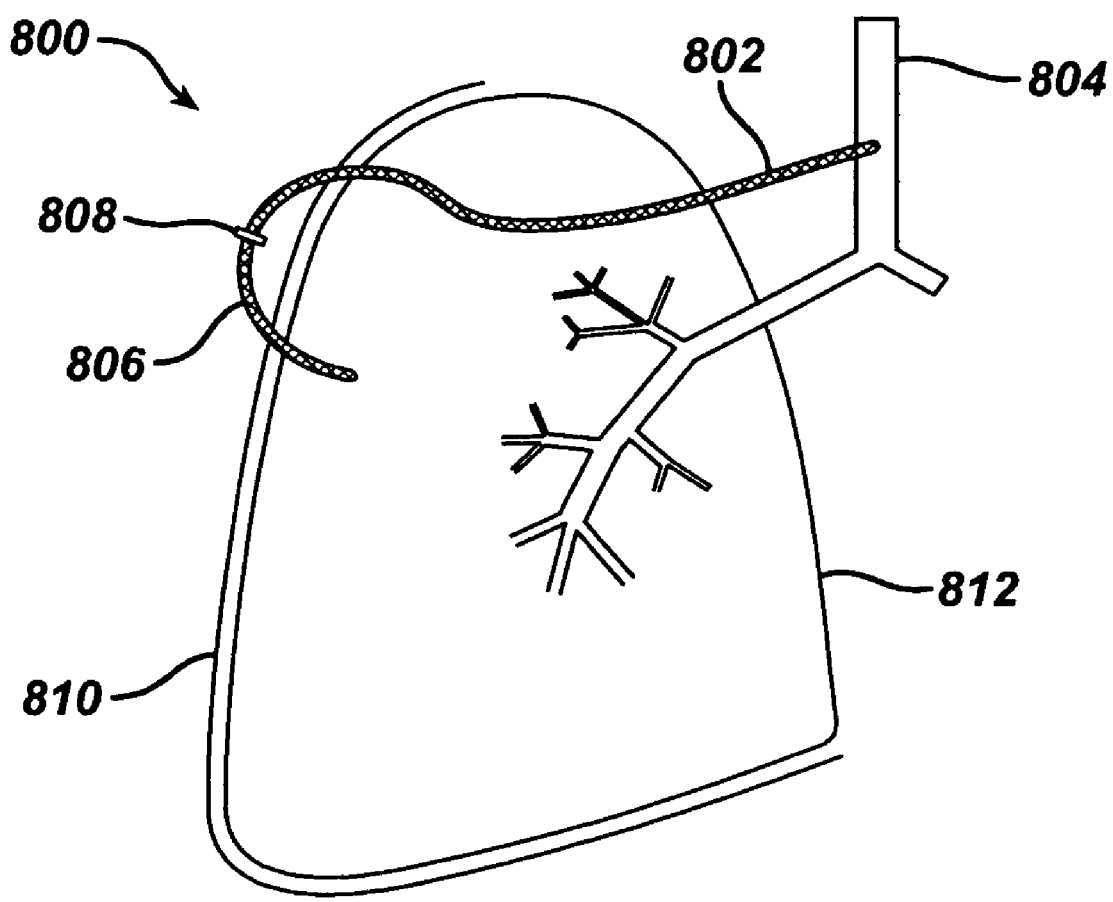
FIG. 8 is a diagrammatic representation of a second exemplary embodiment of a collateral ventilation bypass system in accordance with the present invention.

FIG. 8 illustrates another exemplary collateral ventilation bypass system 800. In this exemplary embodiment, the trachea is utilized to remove trapped air rather than the native airways. As illustrated, a first conduit 802 extends from the patient's trachea 804, or other proximal airways, including the bronchus, to a position external of the patient's body. A second conduit 806 is connected to the first conduit 802 via a fitting 808 and passes through the thoracic wall 810 and passes through the lung 812 at the site determined to have the highest degree of collateral ventilation. If more than one site is determined to have a high degree of collateral ventilation, multiple conduits may be utilized. In operation, when the patient exhales, the pressure in the lungs is greater than the pressure in the trachea 804; accordingly, the air in the highly collaterilized areas of the lung will travel through the first and second conduits 802, 806 to the trachea 804 and out of the patient's nose and mouth with the normally exhaled air.

The first and second conduits 802, 806 may comprise any suitable biocompatible tubing having a resistance to the various gases and other constituents contained in inhaled and exhaled air. As in previously described embodiments, the first and second conduits 802, 806 comprise tubing having an inside diameter in the range from about 1/16 inch to about 1/2 inch, and more preferably from about 1/8 inch to about 1/4 inch.

The connection of the first conduit 802 to the trachea 804 may comprise any suitable airtight seal. For example, a fluid communication between the trachea 804 and the first conduit 802 may be established in a manner identical to that established for a tracheotomy. In addition, as stated above, in order for the collateral ventilation bypass system 800 to function, an airtight seal is preferably maintained where the second conduit 806 passes through the thoracic wall 810 and into the lungs 812. An exemplary method for creating this airtight seal comprises forming adhesions between the visceral pleura of the lung and the parietal pleura. This may be achieved using either chemical methods, including irritants, surgical methods, including pleurectomy or thorascopic talc pleurodesis, or radiotherapy methods, including radioactive gold or external radiation.

The creation of the opening in the thoracic wall may be accomplished in a number of ways. For example, the procedure may be accomplished using an open chest procedure, aternotomy or thoracotomy. Alternately, the procedure may be accomplished using a laproscopic technique, which is less invasive. Regardless of the procedure utilized, the seal should be established while the lung is at least partially inflated in order to maintain a solid adhesive surface. The opening may then be made after the joint has been adequately created between the conduit component and the lung pleural surface. The opening should be adequate in cross-sectional area in order to provide sufficient decompression of the hyperinflated lung. This opening, as stated above, may be created using a number of different techniques such as cutting, piercing, dilating, blunt dissection, radio frequency energy, ultrasonic energy, microwave energy, or cryoblative energy.

The conduits 802, 806 may be sealed to the skin at the sites by any known methods, including those described above with respect to FIGS. 2 through 5. The connection of the extrathoracic component, conduit 806, may comprise a drug, chemical, agent, or other means for preventing or substantially reducing the risk of infection.

The fitting 808 connecting the first and second conduits 802, 806 may comprise any suitable device for creating an airtight seal. The fitting 808 may comprise any type of threaded or non-threaded union, compression fittings similar to compressor type fittings or any other suitable device for establishing an airtight seal and providing for quick release between the two ends of the fitting 808. This type of design would allow easy access for periodic maintenance of the system 800, for example, cleaning the conduits 802, 806. Since the fitting 808 is external to the body, access to the inner body component of the system 800 would be easier. Essentially, access of the system 800 from outside the body would allow for maintenance and diagnosis/observation of the system 800 without subjecting the patient to additional stress and risk. It would also be less time consuming for the doctor.

Figure 9:
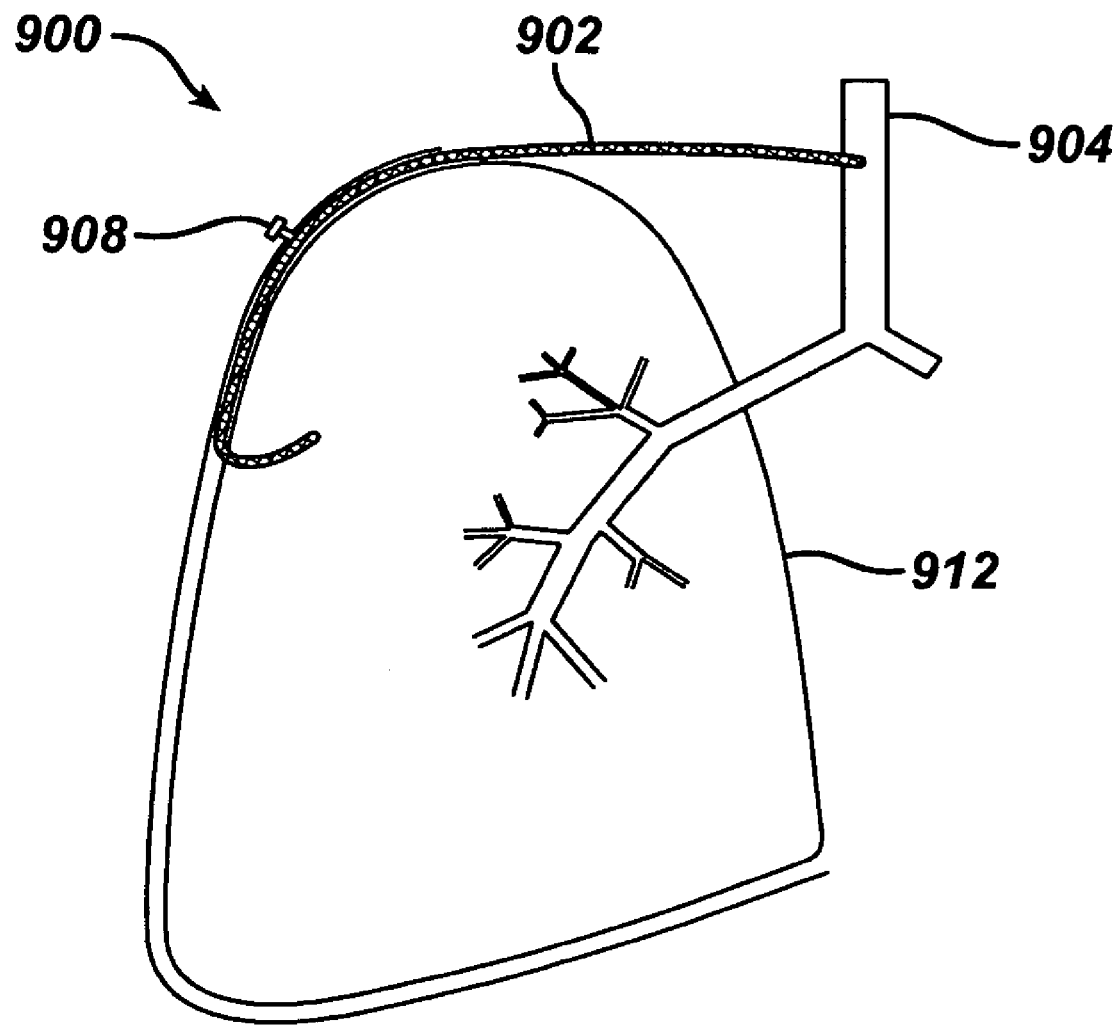
FIG. 9 is a diagrammatic representation of a third exemplary embodiment of a collateral ventilation bypass system in accordance with the present invention.

FIG. 9 illustrates an alternate exemplary embodiment of the exemplary collateral ventilation bypass system 800 described above. In this exemplary embodiment, the system 900 comprises an externally positioned access port 908. As illustrated, a conduit 902 extends from the patient's trachea 904, or other proximal airways, including the bronchus, through a suitable passageway internal to the patient's body and then passes through the lung 912 at the site determined to have the highest degree of collateral ventilation. As set forth above, if more than one site is determined to have a high degree of collateral ventilation, multiple conduits may be utilized. At the desired location within the body, the access port 908 may be placed in-line with the conduit 902 such that at least a portion of the access port 908 is accessible outside of the body. Essentially, the access port 908 should allow the patient or a doctor to open the port and access the system 900 within the patient's body for maintenance and diagnosis/observation of the system 900 as described above.

The access port 908 may comprise any suitable device for providing an airtight seal when closed and easy access to the conduit 902 when open. The access port 908 may comprise various valve arrangements and connectors for connecting other components which may be utilized for various functions. For example, oxygen may be supplied directly to the patient's lungs 912 if needed. In this instance, a valve may be needed to prevent the oxygen from bypassing the lungs 912 and go straight to the trachea 904.

All the remaining components may be the same as described above. In addition, all seals may be accomplished as described above.

Figure 10:
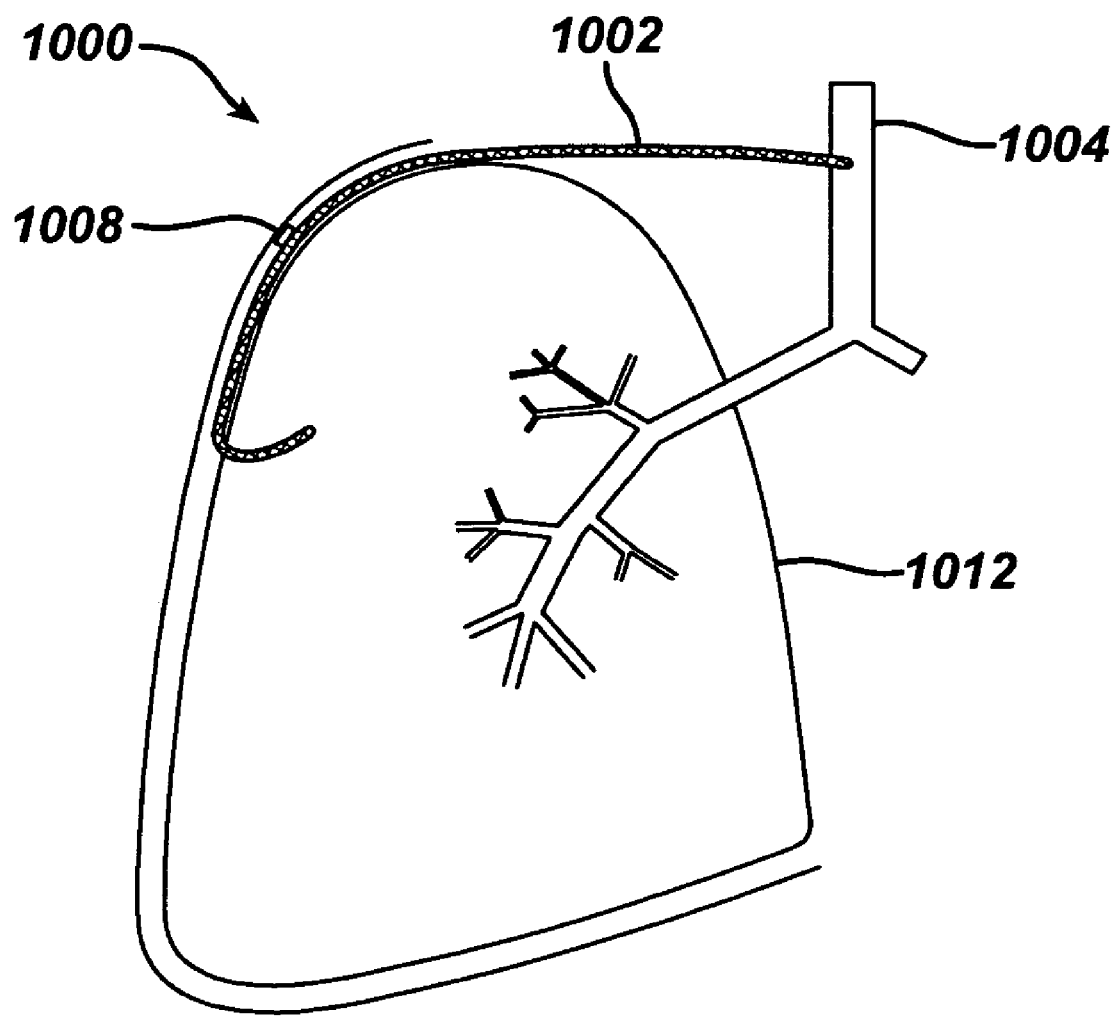
FIG. 10 is a diagrammatic representation of a fourth exemplary embodiment of a collateral ventilation bypass system in accordance with the present invention.

In yet another alternate exemplary embodiment, the extrathoracic access port 908, illustrated in FIG. 9, may be positioned just under the skin so that it is accessible percutaneously. Essentially, the access port would not truly be extrathoracic, but rather just located under the skin and accessible extrathoracically. In this exemplary embodiment access would not be as easily accessible; however, the access point would remain more discrete than the previously described exemplary embodiments. FIG. 10 illustrates this exemplary embodiment.

As illustrated in FIG. 10, the collateral ventilation bypass system 1000 comprises a conduit 1002 that extends from the patient's trachea 1004, or other proximal airways, including the bronchus, through a suitable passageway internal to the patient's body and then passes through the lung 1012 at the site determined to have the highest degree of collateral ventilation. As set forth above, if more than one site is determined to have a high degree of collateral ventilation, multiple conduits may be utilized. At the desired location within the body, an internal access port 1008 may be placed in-line with the conduit 1002. The access port 1008 may comprise any suitable device that allows access via percutaneous means. All remaining components may be the same as described above. In addition, all seals may be accomplished as described above.

It is important to note that in each of the above-described exemplary embodiments, additional components may be added that function to prevent flow from the trachea end of the conduit to the lung. For example, one or more valves may be incorporated throughout the systems to prevent mucus and other substances from entering or re-entering the lung. The main function of the system is to allow exhalation. In theory, patients with emphysema have increased resistance to expiration and not inhalation. Any suitable valves may be utilized, for example, one-way check valves.

As described above, pulmonary emphysema leads to the breakdown of lung tissue, which in turn leads to the reduced ability of the lungs to recoil and the loss of radial support of the airways. Consequently, the loss of elastic recoil of the lung tissue contributes to the inability of individuals to exhale completely. The loss of radial support of the airways also allows a collapsing phenomenon to occur during the expiratory phase of breathing. This collapsing phenomenon also intensifies the inability for individuals to exhale completely. As the inability to exhale completely, increases, residual volume in the lungs also increases. This then causes the lung or lungs to establish in a hyperinflated state where an individual can only take short shallow breaths. Essentially, air is not effectively expelled and stale air accumulates in the lungs. Once the stale air accumulates in the lungs, the individual is deprived of oxygen.

Lung volume reduction surgery is an extremely traumatic procedure that involves removing part or parts of the lung or lungs. By removing the portion of the lung or lungs which is hyperinflated, pulmonary function may improve due to a number of mechanisms, including enhanced elastic recoil, correction of ventilation/perfusion mismatch and improved efficiency of respiratory work. Essentially, as the emphysematous tissue volume is reduced, the healthier tissue is better ventilated. However, lung volume reduction surgery possesses a number of potential risks as described in more detail subsequently.

The collateral ventilation bypass trap system 700, illustrated in FIG. 7, and the collateral ventilation bypass system 800, illustrated in FIG. 8, utilize the collateral ventilation phenomenon to allow the air entrapped in the lung or lungs to bypass the native airways and be expelled either to a containment vessel or to the ambient environment. However, in an alternate exemplary embodiment, a device, which works similarly to collateral ventilation bypass and provides results commensurate with lung volume reduction surgery, is disclosed herein. Essentially, in this exemplary embodiment, the invention is directed to a device and associated method for assisting pulmonary decompression. In other words, the present invention is directed to pulmonary decompression assist device and method that would provide a means for the removal of trapped air in the emphysematous lung and the maintenance of the emphysematous area compressed to a smaller volume, with the result being that healthier lung tissue will have more volume in the thoracic cavity to ventilate. The effects of this device may be similar to that of lung volume reduction surgery.

The exemplary pulmonary decompression assist device of the present invention may be strategically positioned in the body of a patient such that it is in fluid communication with the patient's lung or lungs and the external environment. The device would allow air to be exhaled out from the lung or lungs through the native airways while assisting in removing trapped air in the hyperinflated portion of the lung or lungs. Lung volume reduction surgery is an extremely invasive and traumatic procedure that in a substantially high number of cases causes the patients undergoing the procedure to become excluded from being a candidate for lung transplantation. The device of the present invention provides for a minimally invasive procedure for causing the lung volume to reduce similarly to lung volume reduction surgery while allowing the patient to remain a viable candidate for lung transplantation.

The exemplary pulmonary decompression device may utilize any number of known techniques for creating a sufficient pressure differential between the inside of the lung or lungs and an area external of the lung or lungs to allow the trapped air to exit the lung or lungs. The device may comprise any suitable device such as pumps or fans or any other means to create the pressure differential. If the collateral airflow and areas of emphysema are situated so that air may reinflate that area, the device may be configured to continuously draw air from the lung or lungs to maintain a smaller lung volume of the emphysematous tissue. The device may be left in the patient's body indefinitely in order to maintain the compression of the emphysematous tissue in the lung or lungs. In addition, in order to maintain the cleanliness of the device and the safety of the patient, the device may be constructed as a disposable device and be replaced at various intervals. In addition, portions of the device that are easily accessible may be made disposable. Alternately, the device may be constructed for easy removal, easy cleaning and easy replacement.

Figure 11:
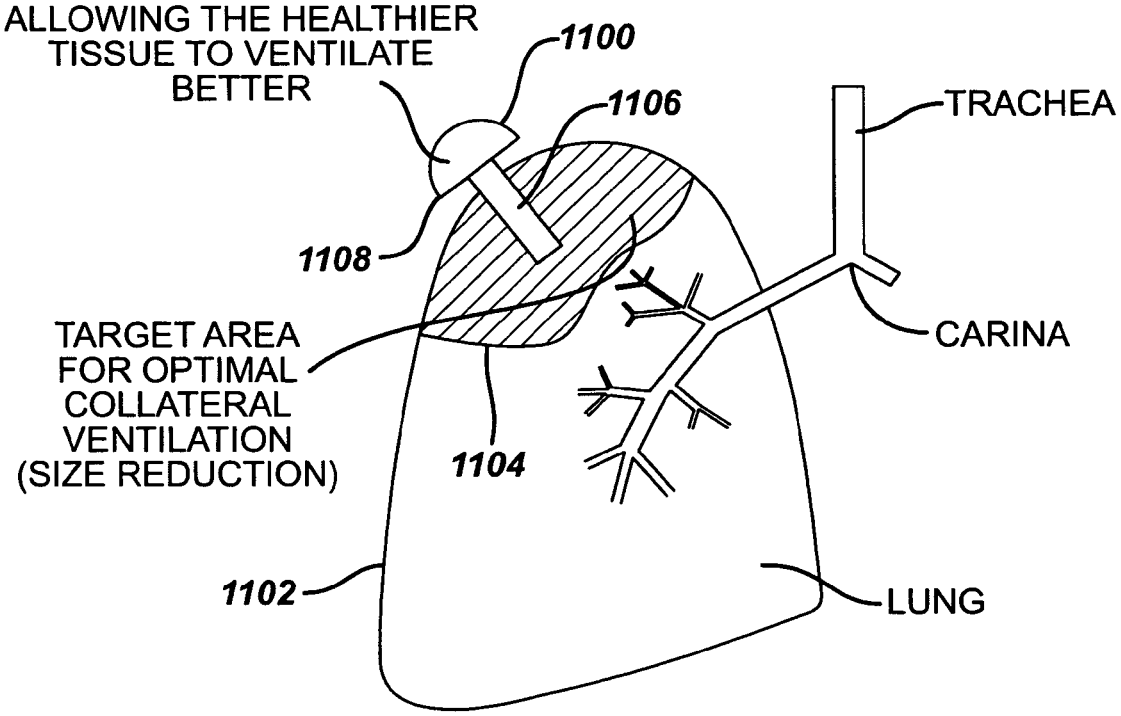
FIG. 11 is a diagrammatic representation of an exemplary pulmonary decompression device in accordance with the present invention.

Referring to FIG. 11, there is illustrated an exemplary pulmonary decompression device 1100 in accordance with the present invention. As described herein, there is generally an optimal location to penetrate the outer pleura of the lung to access the most collaterally ventilated area or areas of the lung and a variety of techniques to locate the area or areas. Once the desired location is determined, the decompression device 1100 may be inserted into the lung 1102. On insertion and placement of the decompression device 1100 into the lung 1102, it is particularly advantageous to establish an airtight seal of the parietal and visceral pleurae. If a proper airtight seal is not created between the decompression device, parietal and visceral pleurae, then a pneumothorax may occur.

It is important to note that one or more devices may be utilized in each lung to remove trapped air from highly collateralized areas. Alternately, a single device with multiple conduits may be utilized. As illustrated in FIG. 11, the decompression device 1100 is placed in the lung 1102 in the area of highest collateral ventilation 1104. In one exemplary embodiment, only a first section 1106 of the decompression device 1100 is positioned within the lung 1102 while a second section 1108 of the decompression device 1100 is secured external to the lung 1102. The sealing of the device 1100 may be made in accordance with any of the devices and methodologies described herein.

At least a portion of the second section 1108 is external to the patient's body. The portion of the second section 1108 that is external to the patient's body may exit the body at any suitable location. In one exemplary embodiment, the portion of the second section 1108 exists the body through the chest and thus may be sealed in accordance with any of the devices and methodologies described herein.

The first section 1106 may comprise any suitable biocompatible material configured to facilitate the flow of air from the lung 1102. For example, the first section 1106 may comprise a conduit similar in size, material and construction as the other conduits described herein. The second section 1108 may be connected to the first section 1106 by any suitable means, including threaded unions or compression type fittings. The second section 1108 comprises a housing for an apparatus that draws air from the hyperinflated portion of the lung 1104 through the first section 1106 and directs it out of the patient's body. The apparatus may include any suitable device for creating a pressure differential between the inside and outside of the lung 1102 such that air will easily flow from the lung 1102. The apparatus may include a miniature pump or fan. The miniature pump or fan may be powered by any suitable means, including batteries or rechargeable batteries. In the above-described exemplary embodiment, the miniature pump or fan and its power supply may be housed completely in the housing. In other alternate exemplary embodiments, one or more of the pump/fan or power supply may be located remotely from the second section 1108. For example, the second section 1108 may simply comprise a second conduit removably connected on one end to the first conduit and on a second end to the apparatus that draws air from the diseased section of the lung 1104.

In the exemplary embodiment illustrated in FIG. 11, the apparatus that draws air from the diseased section of the lung 1104 and its associated power supply are housed within the second section 1108. This design provides the most freedom for the patient. Various known miniature vacuum pumps or fans may be used to continuously draw air from the diseased section of the lung 1104, thereby reducing the emphysematous tissue volume and allowing the healthier tissue to ventilate better. The miniature fan/pump and associated power supply may be separate components or a single component. These miniature devices may comprise microelectromechanical systems or MEMS, or any other suitable device for drawing air from one location and venting it to a second location. The decompression device 1100 should be designed to be easily maintained. For example, the second section 1108 may be made such that it can be removed, the power supply recharged and the other components cleaned and then replaced. Alternately, the second section 1108 may simply be disposable.

The power supply may comprise any suitable means for supplying power continuously for extended periods of time. The power supply may comprise batteries, rechargeable batteries, piezoelectric devices that generate electrical power from mechanical strain or any other suitable device. In addition, other than a fan or pump for creating a vacuum, some type of switching elements may be utilized for creating a slight pressure differential.

Figure 12A:
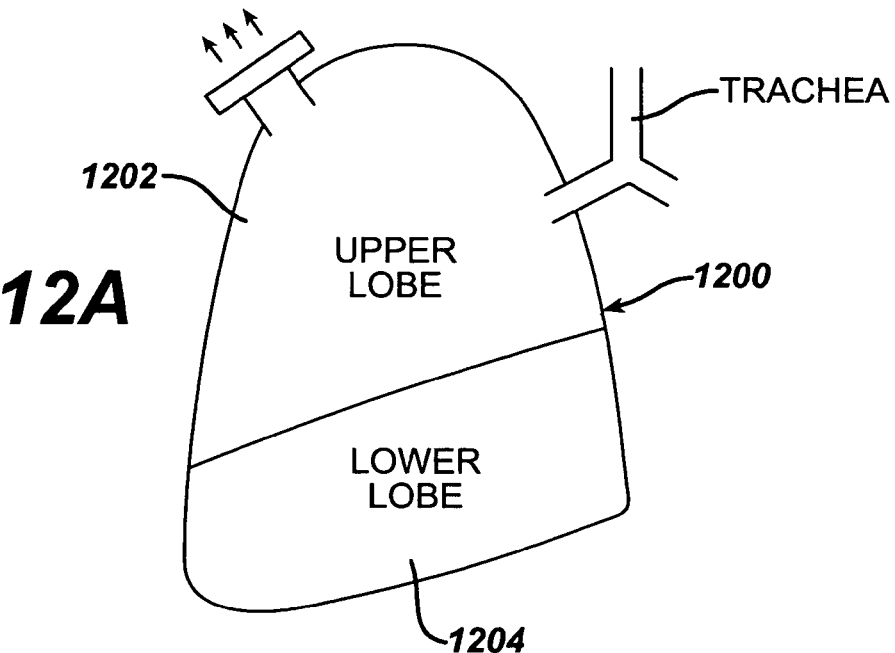
FIGS. 12a and 12b are diagrammatic representations of the effects on lung volume in accordance with the present invention.
Figure 12B:
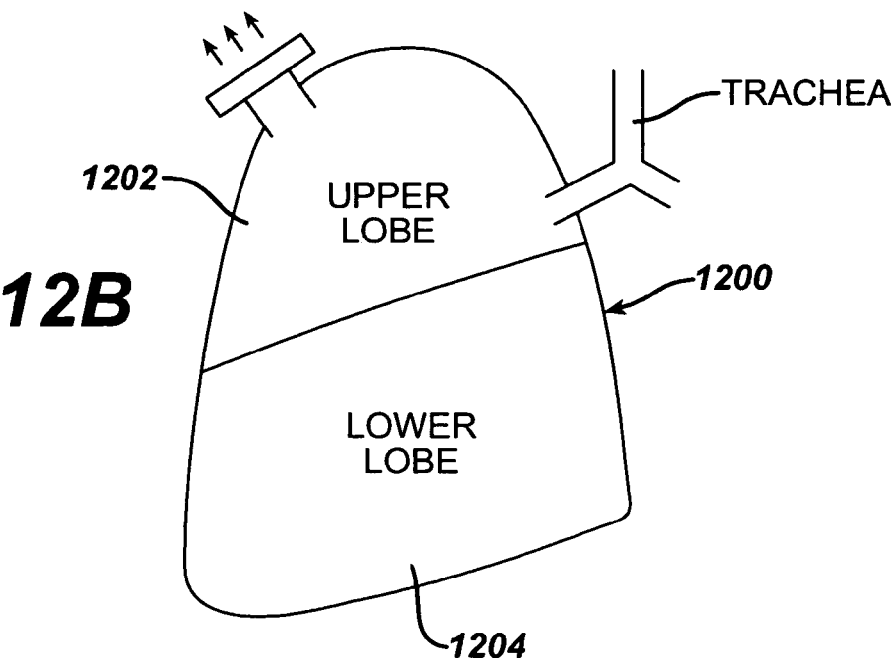

Accordingly, rather than a resection of the lung tissue, the decompression device removes trapped air from the emphysematous section of the lung and maintains the emphysematous section in a compressed state or smaller volume, thereby allowing the healthier lung tissue more volume in the thoracic cavity to ventilate. FIG. 12a illustrates the decompression device 1100 removing air from the hyperinflated portion 1202 of the lung 1200. As illustrated, in this lung, the hyperinflated or emphysematous portion 1202 of the lung 1200 is larger than the healthy section or portion 1204 of the lung 1200. As the device 1100 continues to remove the accumulated or trapped air, the volume of the hyperinflated portion 1202 of the lung 1200 shrinks, thereby allowing the healthier portion 1204 more room to fully ventilate, thereby increasing in volume as illustrated in FIG. 12b.

In an alternate exemplary embodiment, a more passive device may be utilized for reducing the size of the lung. A lung reduction device may be strategically positioned about the body of a patient and access the patient's lung or lungs. The device would allow air to be expelled from the lung or lungs while preventing air from re-entering therethrough. Essentially, the device would comprise at least one component that accesses the outer pleural layer of the emphysematous portion or portions of the patient's lung or lungs. This at least one component will utilize the collateral ventilation of the lung or lungs and allow the entrapped air in the emphysematous portion or portions of the lung or lungs to bypass the native airways and expel through to the outside of the body through a second component. The second component includes a feature that allows air to flow from the lung or lungs to the ambient environment, but not from the ambient environment back into the lung or lungs. If the collateral airflow and areas of emphysema are situated so that air cannot reinflate these portions of the lung or lungs, then a size reduction of that area of the lung should occur.

Figure 13A:
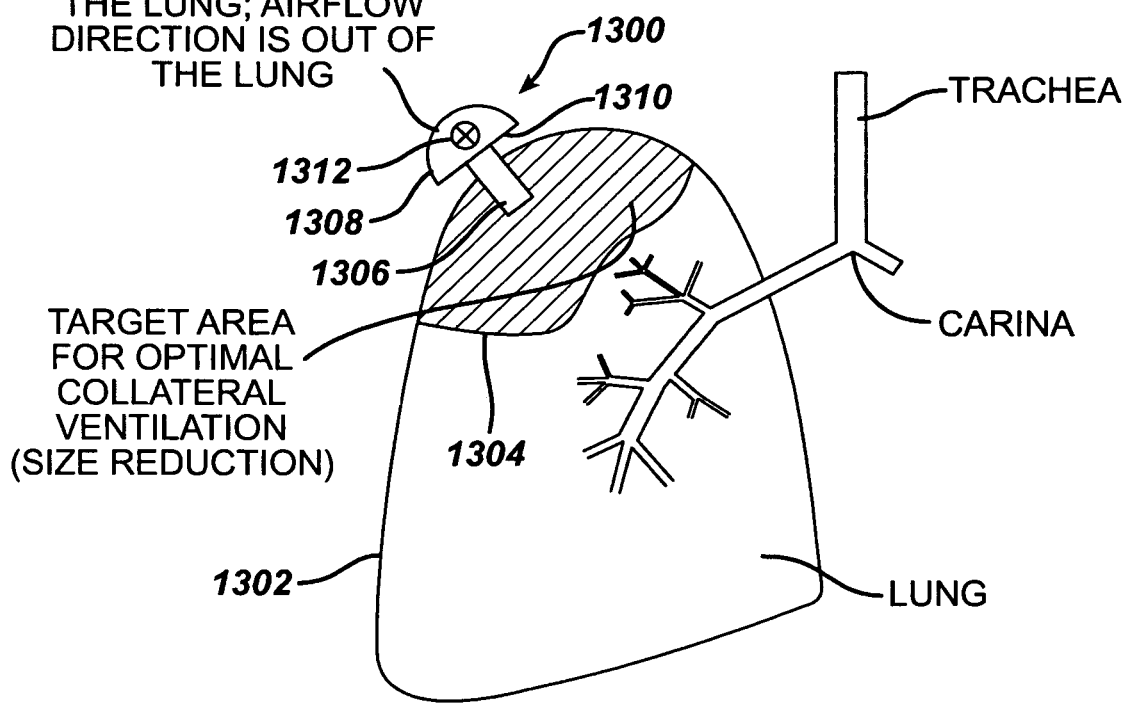
FIGS. 13a and 13b are diagrammatic representations of the effects on lung volume reduction utilizing the lung reduction system in accordance with the present invention.
Figure 13B:
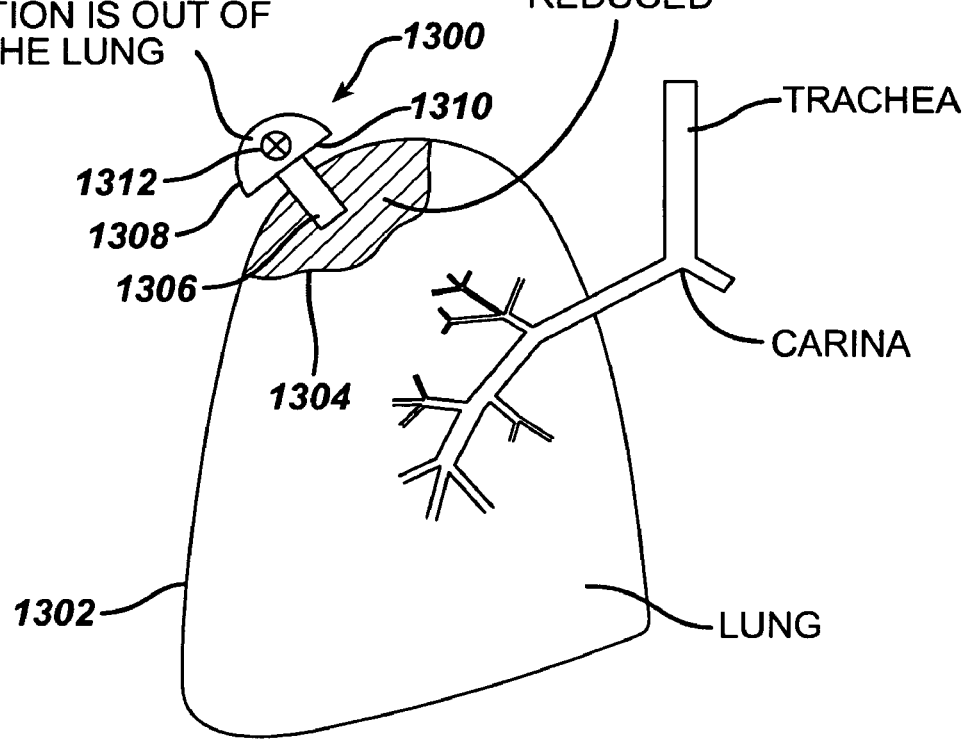

Referring to FIGS. 13a and 13b, there is illustrated an exemplary lung reduction device 1300 in accordance with the present invention. As described herein, there is generally an optimal location to penetrate the outer pleura of the lung to access the most collaterally ventilated area or areas of the lung or lungs and a variety of techniques to locate these areas. Once the desired location or locations are determined, the lung reduction device 1300 may be inserted into the lung 1302. The insertion or introduction of the device 1300 may be accomplished utilizing a number of minimally invasive techniques, for example, percutaneously or endoscopically, thereby substantially reducing the risk to the patient and trauma to the lung or lungs. It is important to note that all of the systems and devices described herein are preferably implanted utilizing minimally invasive techniques. On insertion and placement of the lung reduction device 1300 into the lung 1302, it is particularly advantageous to establish an airtight seal of the parietal and visceral pleurae utilizing any of the techniques, devices and processes described herein. If an airtight seal is not established between the lung reduction device 1300, parietal and visceral pleurae, then a pneumothorax may occur.

It is important to note that one or more lung reduction devices may be utilized in each lung to remove trapped air from highly collateralized areas. Alternately, a single lung reduction device in fluid communication, through conduits or other similar means, with multiple locations may be utilized. For case of explanation, a single device and single diseased portion is described and illustrated. Once again, referring to FIGS. 13a and 13b, the lung reduction device 1300 is implanted in the lung 1302 in the area of highest collateral ventilation 1304. In the exemplary embodiment illustrated, a first section 1306 of the lung reduction device 1300 is positioned within the inner volume of the lung 1302 while a second section 1308 of the lung reduction device 1300 is secured to the patient's body external to the lung 1302. The first section 1306 of the device 1300 accesses the parenchyma of the lung 1302. The parenchyma are the cells in tissues that are concerned with function rather than structure. In other words, the first section 1306 accesses the alveoli of the lung 1302. The attainment of an airtight seal of the lung reduction device 1300 may be made in accordance with any of the devices and methodologies described herein.

At least a portion of the second section 1308 is external to the patient's body. The portion of the second section 1308 that is external to the patient's body may exit or extend from the body at any suitable location. Preferably, the portion of the second section 1308 exits at a location that proves to be of minimum burden to the patient and allows for easy access for maintenance, repair or replacement. In one exemplary embodiment, the portion of the second section 1308 exits the body through the chest and thus may be sealed in accordance with any of the devices and methodologies described herein.

The first section 1306 may comprise any suitable device for facilitating the flow of air from the lung 1302. For example, the first section 1306 may comprise a conduit similar in size, material and construction or any of the other conduits described herein. The second section 1308 may be connected to the first section 1306 by any suitable means, including threaded connectors, unions or compression type fittings.

The second section 1308 may comprise any suitable means for allowing one-way airflow. In one exemplary embodiment, the second section 1308 comprises a housing 1310 and a one-way valve 1312. The housing 1310 may be formed from any suitable biocompatible material. A portion of the housing 1310 houses the one-way valve 1312 while another portion of the housing 1310 forms the portion that is external to the body. The one-way valve 1312 may comprise any suitable pressure actuated valve, which allows air to flow from one lung 1302 to the ambient environment. The one-way valve 1312 may comprise a check valve, a reed valve, needle valves, flapper check valves or any other suitable device. In preferred embodiments, the one-way valve 1312 requires only a slight pressure differential to open and allow air flow from the lung 1302 to the ambient or external environment, but does not allow air flow back into the lung 1302 even under substantial reverse pressure.

In operation, when the person inhales, the volume of the thoracic cavity increases by the contraction of the diaphragm and thus the volume of the lungs also increases. As the volume of the lungs increase, the pressure of the air in the lungs falls slightly below the pressure of the air external to the body and thus air flows through the respiratory passageways into the lungs until the pressure equalizes. When the person exhales, the diaphragm is relaxed, the volume of the thoracic cavity decreases, which in turn decreases the volume of the lungs. As the volume of the lungs decrease, the pressure of the air in the lungs rises slightly above the pressure of the air external to the body. Accordingly, as a result of this slight pressure differential, the air in the alveoli is expelled through the respiratory passageways until the pressure equalizes. However, in the diseased area 1304 of the lung 1302, normal exhalation does not work for the reasons described herein and thus the increased pressure in the lung 1302 opens the one-way valve 1312 and air flows from the diseased portion 1304 through the first section 1306, through the one-way valve 1312 and out of the body.

The lung reduction device 1300 may be left in the lung indefinitely to maintain the compression of the emphysematous tissue lung 1300 as described above with respect to the decompression device. In order to maintain cleanliness and safety, the lung reduction device 1300 or at least portions thereof may be made disposable and thus be replaced at regular intervals or when needed. As the lung reduction device 1300 continues to allow the trapped air to exit the lung 1302, the volume of the hyperinflated or diseased portion 1304 of the lung 1300 shrinks, thereby allowing the healthier portion of the lung 1300 more room to fully ventilate, thereby increasing in volume as illustrated in FIG. 13b.

The lung reduction device 1300 may be left in the body until the area of the compressed emphysematous tissue has permanently compressed, atelectasis. At this point, the lung reduction device 1300 may potentially be removed safely. If healing of the insertion site of the reduction device 1300 has occurred, the fistula created may be permanently sealed.

In the above-described exemplary apparatus and procedure for increasing expiratory flow from a diseased lung using the phenomenon of collateral ventilation, there will be an optimal location to penetrate the outer pleura of the lung to access the most collaterally ventilated area or areas of the lung. In addition, in the above-described exemplary pulmonary decompression assist device, there is an optimal location for decompressing the hyperinflated lung or lungs. As described above, there are a variety of techniques to locate the most collaterally ventilated area or areas of the lungs. Since a device or component of the apparatus functions to allow the air entrapped in the lung to bypass the native airways and be expelled outside of the body, it is particularly advantageous to provide an airtight seal of the parietal (thoracic wall) and visceral (lung) pleurae. If a proper airtight seal is not created between the device, parietal and visceral pleurae, then a pneumothorax (collapsed lung) may occur. Essentially, in any circumstance where the lung is punctured and a device inserted, an airtight seal should preferably be maintained.

One way to achieve an airtight seal is through pleurodesis, i.e. an obliteration of the pleural space. There are a number of pleurodesis methods, including chemical, surgical and radiological. In chemical pleurodesis, an agent such as tetracycline, doxycycline, bleomycin or nitrogen mustard may be utilized. In surgical pleurodesis, a pleurectomy or a thorascopic talc procedure may be performed. In radiological procedures, radioactive gold or external radiation may be utilized. In the present invention, chemical pleurodesis is utilized.

Exemplary devices and methods for delivering a chemical(s) or agent(s) in a localized manner for ensuring a proper airtight seal of the above-described apparatus is described below. The chemical(s), agent(s) and/or compound(s) are used to create a pleurodesis between the parietal and visceral pleura so that a component of the apparatus may penetrate through the particular area and not result in a pneumothorax. There are a number of chemical(s), agent(s) and/or compound(s) that may be utilized to create a pleurodesis in the pleural space. The chemical(s), agent(s) and/or compound(s) include talc, tetracycline, doxycycline, bleomycin and minocycline.

Figure 14:
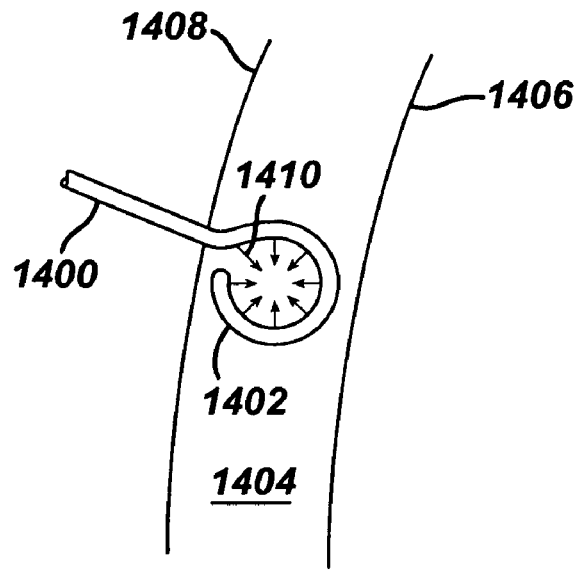
FIG. 14 is a diagrammatic representation of a first exemplary embodiment of a localized pleurodesis chemical delivery system.

In one exemplary embodiment, a modified drug delivery catheter may be utilized to deliver chemical(s), agent(s) and/or compound(s) to a localized area for creating a pleurodesis in that area. In this exemplary embodiment, the pleurodesis is formed and then the conduit 704, as illustrated in FIG. 7, is positioned in the lung 708 through the area of the pleurodesis. The drug delivery catheter provides a minimally invasive means for creating a localized pleurodesis. Referring to FIG. 14, there is illustrated an exemplary embodiment of a drug delivery catheter that may be utilized in accordance with the present invention. Any number of drug delivery catheters may be utilized. In addition, the distal tip of the catheter may comprise any suitable size, shape or configuration thereby enabling the formation of a pleurodesis having any size, shape or configuration.

As illustrated in FIG. 14, the catheter 1400 is inserted into the patient such that the distal end 1402 is positioned in the pleural space 1404 between the thoracic wall 1408 and the lung 1406. In the illustrated exemplary embodiment, the distal end 1402 of the catheter 1400 comprises a substantially circular shape that would allow the chemical(s), agent(s) and/or compound(s) to be released towards the inner diameter of the substantially circular shape as indicated by arrows 1410. The distal end 1402 of the catheter 1400 comprising a plurality of holes or openings 1412 through which the chemical(s), agent(s) and/or compound(s) are released. As stated above, the distal end 1402 may comprise any suitable size, shape or configuration. Once the chemical(s), agent(s) and/or compound(s) are delivered, the catheter 1400 may be removed to allow for implantation of the conduit 704 (FIG. 7). Alternately, the catheter 1400 may be utilized to facilitate delivery of the conduit 704.

The distal end or tip 1402 of the catheter 1400 should preferably maintain its desired size, shape and/or configuration once deployed in the pleural space. This may be accomplished in a number of ways. For example, the material forming the distal end 1402 of the catheter 1400 may be selected such that it has a certain degree of flexibility for insertion of the catheter 800 and a certain degree of shape memory such that it resumes its original or programmed shape once deployed. Any number of biocompatible polymers with these properties may be utilized. In an alternate embodiment, another material may be utilized. For example, a metallic material having shape memory characteristics may be integrated into the distal end 1402 of the catheter 1400. This metallic material may include nitinol or stainless steel. In addition, the metallic material may be radiopaque or comprise radiopaque markers. By having a radiopaque material or radiopaque markers, the catheter 1400 may be viewed under x-ray fluoroscopy and aid in determining when the catheter 1400 is at the location of the highest collateral ventilation.

In another alternate exemplary embodiment, a local drug delivery device may be utilized to deliver the pleurodesis chemical(s), agent(s) and/or compound(s). In this exemplary embodiment, the pleurodesis is formed and then the conduit 704, as illustrated in FIG. 7, is positioned in the lung 708 through the pleurodesis. In this exemplary embodiment, chemical(s), agent(s) and/or compound(s) may be affixed to an implantable medical device. The medical device is then implanted in the pleural cavity at a particular site and the chemical(s), agent(s) and/or compound(s) are released therefrom to form or create the pleurodesis.

Any of the above-described chemical(s), agent(s) and/or compounds) may be affixed to the medical device. The chemical(s), agent(s) and/or compound(s) may be affixed to the medical device in any suitable manner. For example, the chemical(s), agent(s) and/or compound(s) may be coated on the device utilizing any number of well known techniques including, spin coating, spraying or dipping, they may be incorporated into a polymeric matrix that is affixed to the surface of the medical device, they may be impregnated into the outer surface of the medical device, they may be incorporated into holes or chambers in the medical device, they may be coated onto the surface of the medical device and then coated with a polymeric layer that acts as a diffusion barrier for controlled release of the chemical(s), agent(s) and/or compound(s), they may be incorporated directly into the material forming the medical device, or any combination of the above-described techniques. In another alternate embodiment, the medical device may be formed from a biodegradable material which elutes the chemical(s), agent(s) and/or compound(s) as the device degrades.

Figure 15:
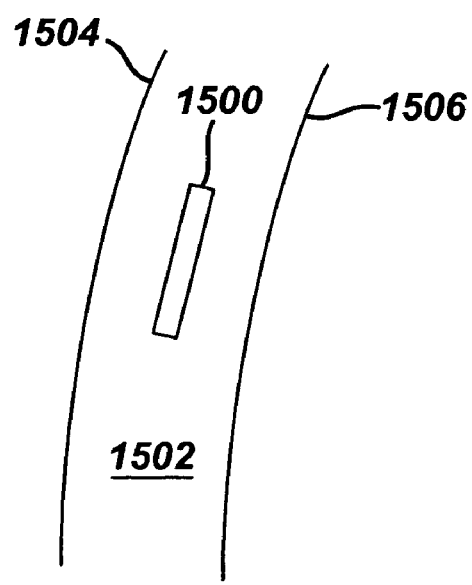
FIG. 15 is a diagrammatic representation of a second exemplary embodiment of a localized pleurodesis chemical delivery system.

The implantable medical device may comprise any suitable size, shape and/or configuration, and may be formed using any suitable biocompatible material. FIG. 15 illustrates one exemplary embodiment of an implantable medical device 1500. In this embodiment, the implantable medical device 1500 comprises a substantially cylindrical disk 1500. The disk 1500 is positioned in the pleural space 1502 between the thoracic wall 1504 and the lung 1506. Once in position, the disk 1500 elutes or otherwise releases the chemical(s), agent(s) and/or compound(s) that form the pleurodesis. The release rate may be precisely controlled by using any of the various techniques described above, for example, a polymeric diffusion barrier. Also, as stated above, the disk 1500 may be formed from a biodegradable material that elutes the chemical(s), agent(s) and/or compound(s) as the disk 1500 itself disintegrates or dissolves. Depending upon the material utilized in the construction of the disk 1500, a non-biodegradable disk 1200 may or may not require removal from the pleural cavity 1502 once the pleurodesis is formed. For example, it may be desirable that the disk 1500 is a permanent implant that becomes integral with the pleurodesis.

As described in the previous exemplary embodiment, the disk 1500 may comprise a radiopaque marker or be formed from a radiopaque material. The radiopaque marker or material allows the disk 1500 to be seen under fluoroscopy and then positioned accurately.

In yet another alternate exemplary embodiment, the fluid characteristics of the chemical(s), agent(s) and/or compound(s) may be altered. For example, the chemical(s), agent(s) and/or compound(s) may be made more viscous. With a more viscous chemical agent and/or compound, there would be less chance of the chemical, agent and/or compound moving from the desired location in the pleural space. The chemical(s), agent(s) and/or compound(s) may also comprise radiopaque constituents. Making the chemical(s), agent(s) and/or compounds radiopaque would allow the confirmation of the location of the chemical(s), agent(s) and/or compound(s) with regard to the optimal location of collateral ventilation.

The chemical(s), agent(s) and/or compound(s) as modified above may be utilized in conjunction with standard chemical pleurodesis devices and processes or in conjunction with the exemplary embodiments set forth above.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An implantable lung reduction device comprising:
at least one first implantable member in fluid communication, at a predetermined site, within a lung of a patient, the at least one implantable member passing through a lung via a passage created therethrough;
a sealing device for establishing an airtight seal between the at least one first implantable member and the lung; and
a second member connected to the at least one first implantable member, the second member comprising an apparatus configured for actively drawing air directly from the lung of the patient to vent to an area external of the lung and preventing air from an area external of the lung from re-entering the lung through the implantable lung reduction device, the second member being secured external of the lung.

2. An implantable lung reduction device comprising:
at least one first implantable member in fluid communication, at a predetermined site, within a lung of a patient, the at least one implantable member passing through a lung via a passage created therethrough;
a first sealing device for establishing an airtight seal between the at least one first member and the lung;
a second member connected to and in fluid communication with the at least one first implantable member, the second member comprising an apparatus configured for allowing air directly from the lung of the patient to vent to the ambient environment, and preventing air from the ambient environment from re-entering the lung through the device, the second member including a section positioned external of the body of the patient; and
a second sealing device for sealing the section positioned external of the body of the patient to the body.

* * * * *